(12) United States Patent
Takimiya et al.

(10) Patent No.: US 8,232,546 B2
(45) Date of Patent: Jul. 31, 2012

(54) FUSED POLYCYCLIC AROMATIC COMPOUND, PROCESS FOR PRODUCING THE SAME, AND USE THEREOF

(75) Inventors: Kazuo Takimiya, Higashi-Hiroshima (JP); Tatsuya Yamamoto, Higashi-Hiroshima (JP)

(73) Assignee: Hiroshima University, Chiyoda-Ku, Tokyo (JP)

( * ) Notice: Subject to any disclaimer, the term of this patent is extended or adjusted under 35 U.S.C. 154(b) by 624 days.

(21) Appl. No.: 12/312,083

(22) PCT Filed: Oct. 22, 2007

(86) PCT No.: PCT/JP2007/070569
§ 371 (c)(1),
(2), (4) Date: Apr. 24, 2009

(87) PCT Pub. No.: WO2008/050726
PCT Pub. Date: May 2, 2008

(65) Prior Publication Data
US 2010/0065826 A1   Mar. 18, 2010

(30) Foreign Application Priority Data
Oct. 25, 2006   (JP) .................................. 2006-290192

(51) Int. Cl.
*H01L 51/00*   (2006.01)
*C07D 495/02*   (2006.01)
*C07D 517/02*   (2006.01)

(52) U.S. Cl. ....... 257/40; 549/41; 562/899; 257/E51.05; 313/504; 428/917

(58) Field of Classification Search .................... 549/41, 549/456; 562/899
See application file for complete search history.

(56) References Cited

U.S. PATENT DOCUMENTS

| 2003/0073725 A1 | 4/2003 | Baker et al. |
| 2009/0001357 A1 | 1/2009 | Takimiya et al. |
| 2009/0043113 A1* | 2/2009 | Park et al. ........................ 549/41 |

FOREIGN PATENT DOCUMENTS

| EP | 1 138 328 | 10/2001 |
| EP | 1847544 | 10/2007 |
| JP | 2001-261794 | 9/2001 |
| JP | 2003-528856 | 9/2003 |
| JP | 2005-320299 | 11/2005 |
| JP | 2008-010541 | 1/2008 |
| JP | 2008-10541 A * | 1/2008 |
| WO | WO 2006/031893 | 3/2006 |
| WO | WO 2006/077888 | 7/2006 |

OTHER PUBLICATIONS

International Preliminary Report on Patentability (translation) for PCT/JP2007/070569.

Horton, A. Wesley, "The Mechanism of the Reactions of Hydrocarbons with Sulfur" J. Org. Chem1949, vol. 14, No. 5, p. 761-770.
Japanese Office Action together with its English translation for Japanese Patent Application No. 2008-540982 dated Nov. 11, 2011.
Machine translation of JP 2008-010541 (Jan. 17, 2008).
Pavel Pihera et al., "Diels-Alder reactions of [1] benzothieno [3,2-b]furan" Collection of Czechoslovak Chemical Communications, 1998, vol. 63, No. 5, p. 681-697.
L. Christiaens et al., "Synthese d' Alkylchalcogenobenzenes Ortho-Substitués par Ortho-Lithiation" ("Synthesis of ortho-substituted alkylchalcogenobenzenes by ortholithiation") Chemica Scripta, 1984, vol. 24, No. 4-5, p. 178-184.
Friedmann, Walter, "Einwirkung von Schwefel auf β-Methyl-naphthalin unter Druck" ("Action of sulfur on β-methylnaphthalene under pressure") Berichte der Deutschen Chemischen Gesellscghaft, 1916, vol. 49, p. 1352-1355, and English abstract thereof.
Yasuhiro Mazaki et al., "Synthesis of Tetrathieno-Acene and Pentathieno-Acene: UV-Spectral Trend in a Homologous Series of Thieno-Acenes" Tetrahedron Letters, 1989, vol. 30, No. 25, p. 3315-3318.
Kobayashi, Keiji, "Sulfur Heterocycles for Organic Conductors and Superconductors" Phosphorus Sulfur and Silica, vol. 43/1-2, p. 187-208, (1989).
Yasuhiro Mazaki et al., "Crystal and Molecular Structure of Thieno [2'',3'':4',5']thieno[2',3'-$d$]thieno-[3,2-$b$]thiophene as a Hydrogen-poor Heterocycle" J. Chem. Soc. Perkin Trans. 2, 1992, p. 761-764.
Yasuhiro Mazaki et al., "An Even-Odd Effect in Inclusion Properties and Crystal Structures of a New Host Series Based on Linearly Condensed Polythiophenes" J. Chem. Soc., Chem. Commun., 1992, p. 1381-1383.
Yasuhiro Mazaki et al."Clathrate Crystals including the 4-Amino-2,2,6,6-tetramethylpiperidine 1-Oxyl (ATEMPO) Radical as a Guest Component: Change of Magnetic Properties with Host Compounds" J. Chem. Soc., Chem. Commun., 1992, p. 1661-1663.
Xinnan Zhang et al., "Effect of Ring Fusion on the Electronic Absorption and Emission Properties of Oligothiophenes" J. Org. Chem., 2003, 68, p. 9813-9815.

(Continued)

*Primary Examiner* — Marie R. Yamnitzky
(74) *Attorney, Agent, or Firm* — Harness, Dickey & Pierce, P.L.C.

(57) ABSTRACT

In one embodiment of the present invention, a novel fused polycyclic aromatic compound of the present invention is (a) a compound including a benzodichalcogenophenobenzod-ichalcogenophene (BXBX) skeleton further having an aromatic ring(s) located outside the BXBX skeleton, or (b) a compound including a BXBX skeleton in which a benzene ring is substituted with a heterocyclic ring. The compound can strengthen intermolecular interaction due to greater π electron orbits. This improves an electron field effect mobility of an organic semiconductor device that is manufactured by use of the compound as an organic semiconductor material. Further, since the number of fused rings included in the compound is small, the compound does not cause problems that generally occur in compounds having an extremely large number of fused rings, i.e., poor solubility in solvent and poor atmospheric stability due to high affinity to oxygen. As a result, the fused polycyclic aromatic compound of the present invention can be preferably used as an organic semiconductor material.

17 Claims, 5 Drawing Sheets

OTHER PUBLICATIONS

Xinnan Zhang et al., "Synthesis and Structure of Fused α-Oligothiophenes with up to Seven Rings" J. Am. Chem. Soc. 2005, 127, p. 10502-10503.

Kai Xiao et al., "A Highly π-Stacked Organic Semiconductor for Field-Effect Transistors Based on Linearly Condensed Pentathienoacene" J. Am. Chem. Soc. 2005, 127, p. 13281-13286.

Kenichi Oyaizu et al., "Linear Ladder-Type π-Conjugated Polymers Composed of Fused Thiophene Ring Systems" Macromolecules 2004, 37, p. 1257-1270.

Toshihiro Okamoto et al., "General Synthesis of Thiophene and Selenophene-Based Heteroacenes" Org. Lett. 2005, vol. 7, No. 23, p. 5301-5304.

Kenichi Kudoh et al., "Reactions of Fused Polycyclic 1,2-Dithiins with Transition Metals: Synthesis of Heteroacenes via Desulfurization" Organometallics 2006, 25, p. 2374-2377.

Takimiya, K., et al. (2006) "2,7-Diphenyl[1]benzoselenopheno[3,2-b][1]benzoselenophene as a Stable Organic Semiconductor for High-Performance Field-Effect transistor" J. Am Chem. Soc, vol. 128, No. 9, pp. 3044-3050.

European Search Report for Application No. 07830303.9 with a mail date of Apr. 23, 2012.

* cited by examiner

FUSED POLYCYCLIC AROMATIC COMPOUND, PROCESS FOR PRODUCING THE SAME, AND USE THEREOF

TECHNICAL FIELD

The present invention relates to a novel fused polycyclic aromatic compound, a method for producing the compound, and a use of the compound. More specifically, the present invention relates to (i) a novel fused polycyclic aromatic compound which has electrical, electronic, or photoelectronic properties, and which can be used as a highly soluble organic semiconductor material, (ii) a method for easily producing the compound, and (iii) a use of the compound.

BACKGROUND ART

In recent years, thin film devices that employ organic semiconductors such as an organic EL device, an organic FET device, and an organic thin film converting device have been considered noteworthy, and some of the thin film devices have been put into practical use. A fundamental and important property of the organic semiconductors for use in these thin film devices is electron field-effect mobility (carrier mobility).

For example, in organic EL devices, the electron field-effect mobility affects charge transport efficiency and is important to realize highly efficient light emission and a low voltage drive. Further, in organic FET devices, the electron field-effect mobility directly affects switching speed and performances of a device to be driven. Therefore, for practical use of the organic FET devices, it is quite important to improve the electron field-effect mobility.

Generally, such organic semiconductors have a low electron field-effect mobility compared with silicon semiconductors, and this prevents practical use of the organic semiconductors. However, recent developments of new organic semiconductor materials have realized organic semiconductors having as high an electron field-effect mobility as that of amorphous silicon.

As the organic semiconductor materials, a material using an existing compound and a material in which an existing compound is modified are conventionally used. For example, polyacene such as pentacene is used as a material of a semiconductor layer. In such an acene material, which is a fused polycyclic aromatic compound, a greater number of fused rings (fused-ring number) provides a better electron field-effect mobility to an organic semiconductor using the material. This is because this provides greater π electron orbits thereby strengthening an intermolecular interaction. In view of this, the increase of the fused-ring number is an effective method to improve the electron field-effect mobility of the organic semiconductors.

However, the increase of the fused-ring number makes it difficult to dissolve the material of a semiconductor layer, or causes a decrease in stability. Although the problem of solubility does not become a significant problem for a deposition material, the remarkable decrease in stability in the atmosphere is a significant hindrance to practical use of the material. In view of this, there is demand for a new material design for solving these problems.

Inventors of the present invention have already found a benzodichalcogenophenobenzodichalcogenophene (hereinafter, referred to as "BXBX") material. As disclosed in Patent Literature 1, the BXBX material successfully has a high stability and a transistor characteristic (high electron field-effect mobility, large on/off ratio, low threshold and swing).

In order to produce a material having more fused rings and find a more excellent material by extending the above finding, it is also an option to produce (a) a compound including: a BXBX skeleton further having an aromatic ring outside the BXBX skeleton, or (b) a compound including a BXBX skeleton in which a benzene ring is substituted with a heterocyclic ring. For example, Patent Literatures 2 and 3, and Non Patent Literatures 1 through 11 disclose methods for producing the compound including a BXBX skeleton in which a benzene ring is substituted with a heterocyclic ring.

Non Patent Literature 12 discloses a compound represented by Formula (2) of the present invention, where $X^1$ and $X^2$ are sulfur atoms, and $R^1$ through $R^{12}$ are hydrogen atoms. However, Non Patent Literature 13 discloses that the structural formula of the compound is erroneously recited in Non Patent Literature 12, and the compound is a structural isomer of Formula (2) of the present invention.

However, the conventional methods disclosed in Patent Literatures 2 and 3, and Non Patent Literatures 1 through 11 needs multistage synthesis in which molecules are required to be built up via multiple stages. Therefore, these methods are too troublesome for practical use. That is, there has not been yet established a method for easily producing an organic semiconductor material that can attain a sufficient electron field-effect mobility.

CITATION LIST

Patent Literature 1
International Publication No. 2006-077888 pamphlet (Publication Date: Jul. 27, 2006)
Patent Literature 2
Japanese Patent Application Publication, Tokukai, No. 2001-261794 A (Publication Date: Sep. 26, 2001)
Patent Literature 3
International Publication No. 2006-031893 pamphlet (Publication Date: Mar. 23, 2001)
Non Patent Literature 1
Mazaki, Y.; Kobayashi, K., Tetrahedron Lett. 1989, 30, 3315-3318.
Non Patent Literature 2
Kobayashi, K. Phosp. Sulf., Silicon and the Related Elements 1989, 43, 187-208.
Non Patent Literature 3
Mazaki, Y.; Kobayashi, K., J. Chem. Soc., Perkin Trans. 2, 1992, 761-764.
Non Patent Literature 4
Mazaki, Y.; Hayashi, N.; Kobayashi, K., J. Chem. Soc., Chem. Commun. 1992, 1381-1383.
Non Patent Literature 5
Mazaki, Y.; Awaga, K.; Kobayashi, K., J. Chem. Soc., Chem. Commun. 1992, 1661-1663.
Non Patent Literature 6
Zhang, X.; Matzger, A. J., J. Org. Chem. 2003, 68, 9813-9815.
Non Patent Literature 7
Zhang, X.; Cote, A. P.; Matzger, A. J. j, J. Am. Chem. Soc. 2005, 127, 10502-10503.
Non Patent Literature 8
Xiao, K.; Liu, Y.; Qi, T.; Zhang, W.; Wang, F.; Gao, J.; Qiu, W.; Ma, Y.; Cui, G.; Chen, S.; Zhan, X.; Yu, G.; Qin, J.; Hu, W.; Zhu, D., J. Am. Chem. Soc. 2005, 127, 13281-13286.
Non Patent Literature 9
Oyaizu, K.; Iwasaki, T.; Tsukahara, Y.; Tsuchida, E., Macromolecules 2004, 37, 1257-1270.
Non Patent Literature 10
Okamoto, T.; Kudoh, K.; Wakamiya, A.; Yamaguchi, S., Org. Lett. 2005, 7, 5301-5304.
Non Patent Literature 11
Kudoh, K.; Okamoto, T.; Yamaguchi, S., Organometallics 2006, 25, 2374-2377.
Non Patent Literature 12
Horton, A. W., J. Org. Chem., 1949, 14, 761-770.

Non Patent Literature 13
Murthy, T. S.; Pandya, L. J.; Tilak, B. D., J. Sci. Industr. Res., 1961, 20B, APRIL, 169-176.

SUMMARY OF INVENTION

The present invention is accomplished in view of the problems. An object of the present invention is to provide: a compound which has electrical, electronic, or photoelectronic properties, and which can be used as a semiconductor material; a simple method for producing the compound; and a use of the compound. More specifically, an object of the present invention is to provide (i) a novel fused polycyclic aromatic compound including: a BXBX skeleton further having an aromatic ring(s) outside the BXBX skeleton and a novel fused polycyclic aromatic compound including a BXBX skeleton in which a benzene ring is substituted with a heterocyclic ring, (ii) a method for producing the compounds, and (iii) use of the compounds.

In order to achieve the object, a compound of the present invention includes: a benzodichalcogenophenobenzodichalcogenophene skeleton having benzene rings; and another benzene ring(s), the compound has a structure in which at least one of the benzene rings of the benzodichalcogenophenobenzodichalcogenophene skeleton being fused to the another benzene ring(s). The benzodichalcogenophenobenzodichalcogenophene skeleton is represented by General Formula (1):

Chem. 1

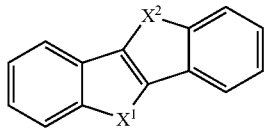

(1)

wherein $X^1$ and $X^2$ are independently a chalcogen atom: and a hydrogen atom of each of the benzene rings may be substituted with an atom or a functional group selected from the group consisting of a halogen atom, an alkyl group, an alkenyl group, an alkynyl group, an aryl group, an alkyloxy group, and alkylthio group. In a case where both $X^1$ and $X^2$ are sulfur atoms, the compound represented by General Formula (1) is a compound represented by General Formula (2):

Chem. 2

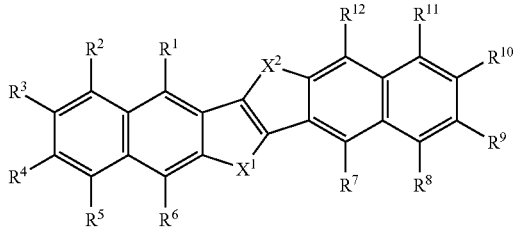

(2)

wherein $R^1$ through $R^{12}$ are independently at least one atom or functional group selected from the group consisting of a hydrogen atom, a halogen atom, an alkyl group, an alkenyl group, an alkynyl group, an aryl group, an alkyloxy group, and an alkylthio group.

It is preferable that the compound of the present invention be represented by General Formula (2):

Chem. 3

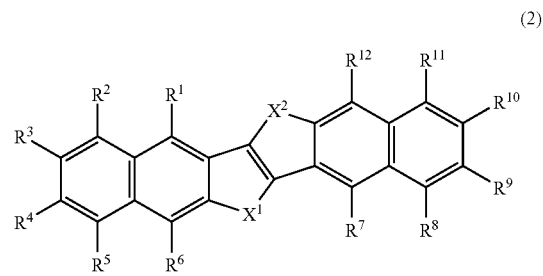

(2)

wherein $X^1$ and $X^2$ are independently a chalcogen atom; and $R^1$ through $R^{12}$ are independently at least one atom or functional group selected from the group consisting of a hydrogen atom, a halogen atom, an alkyl group, an alkenyl group, an alkynyl group, an aryl group, an alkyloxy group, and an alkylthio group.

It is preferable that the compound of the present invention be represented by General Formula (3):

Chem. 4

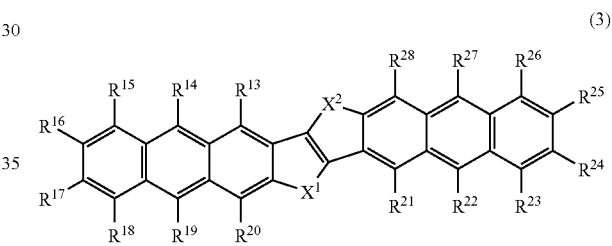

(3)

wherein $X^1$ and $X^2$ are independently a chalcogen atom; and $R^{13}$ through $R^{28}$ are independently at least one atom or functional group selected from the group consisting of a hydrogen atom, a halogen atom, an alkyl group, an alkenyl group, an alkynyl group, an aryl group, an alkyloxy group, and an alkylthio group.

It is preferable that the compound of the present invention be represented by General Formula (4):

Chem. 5

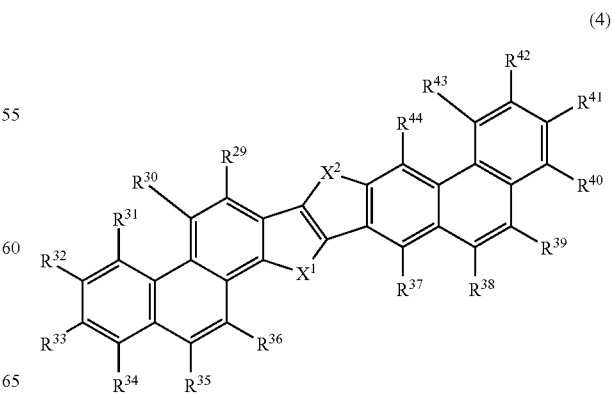

(4)

wherein $X^1$ and $X^2$ are independently a chalcogen atom; and $R^{29}$ through $R^{44}$ are independently at least one atom or functional group selected from the group consisting of a hydrogen atom, a halogen atom, an alkyl group, an alkenyl group, an alkynyl group, an aryl group, an alkyloxy group, and an alkylthio group.

It is preferable that the compound represented by General Formula (5):

Chem. 6

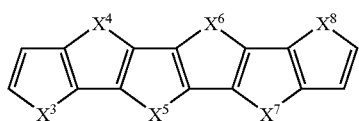

(5)

wherein $X^3$ through $X^8$ are independently a chalcogen atom.

Each of the compounds represented by General Formulae (1) through (5) is either (a) a compound including: a BXBX skeleton further having an benzene ring(s) outside the BXBX skeleton, or (b) a compound including a BXBX skeleton in which a benzene ring is substituted with a heterocyclic ring. Since such novel fused polycyclic aromatic compounds have more fused rings than a BXBX has, these compounds can increase an intermolecular interaction due to greater π electron orbits. In a case where the compounds are used as a material of an organic semiconductor device, the electron field-effect mobility of the organic semiconductor can be improved. From this reason, these compounds of the present invention can be used as very useful materials to develop a new organic semiconductor device.

Even though the fused polycyclic aromatic compounds have a number of fused rings, the compounds do not cause a problem that generally occurs in compounds having an extremely large number of fused rings, i.e., poor atmospheric stability due to high affinity to oxygen. As a result, the fused polycyclic aromatic compounds of the present invention can be preferably used as organic semiconductor materials.

In order to achieve the object, a method of the present invention is to produce a compound represented by General Formula (7):

Chem. 8

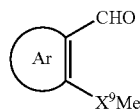

(7)

and the method includes the steps of (i) adding an alkyl metal reagent to a compound represented by General Formula (6):

Chem. 7

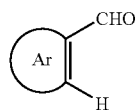

(6)

and (ii) after the step (i), adding a liquid reagent containing chalcogen atoms thereto, wherein in the formulae, $X^9$ is a chalcogen atom; and each Ar is a structure selected from the group consisting of the following chemical structures (a) through (c):

(a) a chemical structure having at least one benzene ring to fuse, in which a hydrogen atom may be substituted with an atom or a functional group selected from the group consisting of a halogen atom, an alkyl group, an alkenyl group, an alkynyl group, an aryl group, an alkyloxy group, and an alkylthio group;

(b) a chemical structure having at least one five-membered ring to fuse, represented by General Formula (9):

Chem. 9

(8)

and (c) a chemical structure represented by General Formula (9):

Chem. 10

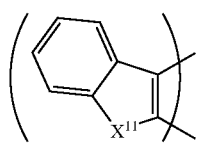

(9)

wherein $X^{10}$ and $X^{11}$ are a chalcogen atom.

In the above method, after the alkyl metal reagent is added to the compound represented by General Formula (6), the liquid reagent containing chalcogen atoms is added thereto. That is, after an ortho-hydrogen in the compound represented by General Formula (6) has been metallated, a chalcogen atom is efficiently introduced into the compound represented by General Formula (6), thereby resulting in that the compound represented by General Formula (7) can be effectively produced. The compound represented by General Formula (7) is a reaction intermediate of a compound represented by General Formula 16, which will be described later. In other words, the compound represented by General Formula (7) can be preferably used as a material of the fused polycyclic aromatic compound(s).

In the production method, it is preferable that each Ar are independently a chemical structure selected from the group consisting of chemical structures (A) through (F):

(A) a chemical structure represented by General Formula (10):

Chem. 11

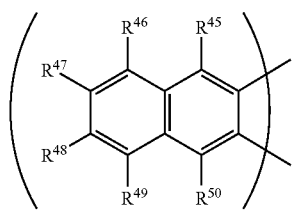

(10)

(B) a chemical structure represented by General Formula (11):

Chem. 12

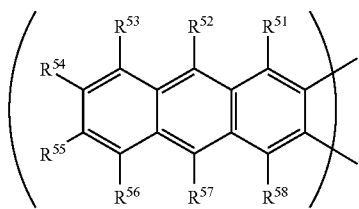

(11)

(C) a chemical structure represented by General Formula (12):

Chem. 13

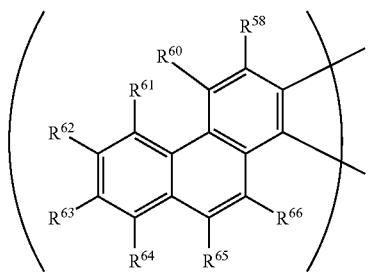

(12)

(D) a chemical structure represented by General Formula (13):

Chem. 14

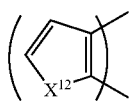

(13)

(E) a chemical structure represented by General Formula (14):

Chem. 15

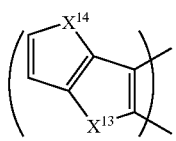

(14)

and (F) a chemical structure represented by General Formula (15):

Chem. 16

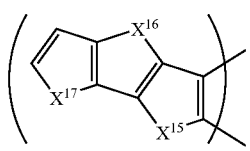

(15)

wherein $X^{12}$ through $X^{17}$ are independently a chalcogen atom; and $R^{45}$ through $R^{66}$ are independently at least one atom or functional group selected from the group consisting of a hydrogen atom, a halogen atom, an alkyl group, an alkenyl group, an alkynyl group, an aryl group, an alkyloxy group, and an alkylthio group.

The compound represented by General Formula (6) in which Ar has a chemical structure selected from the group consisting of the foregoing chemical structures (A) through (F) is easily available, which can readily carry out the aforementioned production method.

A method of the present invention is preferably to produce a compound represented by Formula (17):

Chem. 18

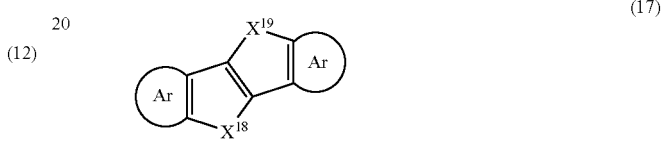

(17)

and the method includes the steps of: (i) reacting compounds represented by General Formula (7) with each other, which compounds are obtained by the aforementioned production method, so as to obtain a compound represented by General Formula (16):

Chem. 17

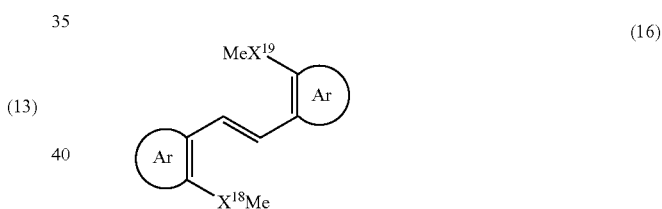

(16)

and (ii) after the step (i), adding iodine to the obtained compound represented by General Formula (16) so as to react with each other, wherein in the formulae, $X^{18}$ and $X^{19}$ are independently a chalcogen atom; and each Ar is a structure selected from the group consisting of the following chemical structures (a) through (c):

(a) a chemical structure having at least one benzene ring to fuse, in which a hydrogen atom may be substituted with an atom or a functional group selected from the group consisting of a halogen atom, an alkyl group, an alkenyl group, an alkynyl group, an aryl group, an alkyloxy group, and an alkylthio group;

(b) a chemical structure having at least one five-membered ring to fuse, represented by General Formula (8):

Chem. 19

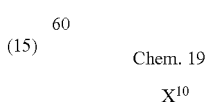

(8)

and (c) a chemical structure represented by General Formula (9):

Chem. 20

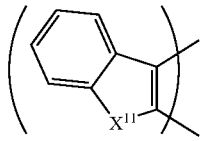
(9)

wherein X" and X" are a chalcogen atom.

The above production method makes it possible to easily produce, without multistage reaction, (a) a compound including: a BXBX skeleton further having an aromatic ring(s) located outside the BXBX skeleton, or (b) a compound including a BXBX skeleton in which a benzene ring is substituted with a heterocyclic ring. Further, in the aforementioned method, impurities are hardly mixed into the obtained compound, thereby making it possible to obtain a highly pure compound.

In the production method of the present invention, it is preferable that the liquid reagent containing chalcogen atoms be dimethyl sulfide or dimethyl diselenide.

The dimethyl sulfide and dimethyl diselenide can easily react with the compound represented by General Formula (6). This makes it possible to easily produce the compound represented by General Formula (7).

An organic semiconductor material of the present invention includes at least one of the compounds represented by General Formulae (1) through (5) and the compounds obtained by the aforementioned production methods.

Since these compounds are fused polycyclic aromatic compounds having more fused rings than a BXBX has, the compounds can increase an intermolecular interaction due to greater π electron orbits. From this reason, the organic semiconductor material has a high electron field-effect mobility. Further, even though the compounds have a number of fused rings, the compounds do not cause a problem that generally occurs in a compound having an extremely large number of fused rings, i.e., poor atmospheric stability due to high affinity to oxygen. As a result, the organic semiconductor material has the atmospheric stability and is excellent in electrical, electronic, or photoelectronic properties.

An organic semiconductor device of the present invention includes the organic semiconductor material.

The arrangement allows the organic semiconductor device to have a high electron field-effect mobility. Further, a device obtained by use of the compound(s) of the present invention can be operated in the atmosphere without a significant decrease in its performance.

It is preferable that the organic semiconductor device be a thin film transistor including an organic semiconductor layer.

The thin film transistor can be broadly used as a switching transistor for switching pixels constituting a display, a signal driver circuit element, a memory circuit element, a signal processing circuit element, and the like. When the organic semiconductor device is a thin film transistor, it is possible to attain downsizing and lightweighting of the organic semiconductor device because a film is formed thin, thereby making it possible to simplify production processes and largely reduce costs of devices and the like necessary for production.

It is preferable that the organic semiconductor device be a light-emitting device including an organic carrier transporting layer and/or a light-emitting layer.

In the arrangement, since the light-emitting device has an organic carrier transporting layer, carriers freely move in the transporting layer. This allows easy formation of electrodes and the like in producing the light-emitting device.

Further, the presence of the light-emitting layer can provide a place where holes injected from an anode and electrons injected from a cathode are recombined while a voltage is being applied.

In addition, when the organic semiconductor device includes both the organic carrier transporting layer and the light-emitting layer, free movement of carriers in the transporting layer can transport holes injected from an anode and electrons injected from a cathode to the light-emitting layer while a voltage is being applied. This can cause the organic semiconductor device to emit light.

It is preferable that the organic semiconductor device has an electron field-effect mobility of not less than 1.0 $cm^2V^{-1}s^{-1}$.

The electron field-effect mobility of not less than 1.0 $cm^2V^{-1}s^{-1}$ allows an organic semiconductor device to highly efficiently emit light, to be driven at a low voltage, and to have an excellent switching speed.

It is preferable that the organic semiconductor device has an on/off current ratio of not less than $10^5$.

Since the on/off current ratio is not less than $10^5$, a ratio between an on current and an off current is large, which causes a current to be large in an on state in which the largest current flows between a source and a drain, thereby resulting in that a high-performance organic semiconductor device can be provided.

Moreover, in the organic semiconductor device of the present invention, it is preferable that the thin film transistor be a bottom-contact type field effect transistor.

With the arrangement, it is possible to form source electrodes and drain electrodes. This makes it possible to provide a field effect transistor that can be highly precise.

Further, in the organic semiconductor device of the present invention, it is preferable that the thin film transistor be a top-contact type field effect transistor.

REFERENCE SIGNS LIST

Figure 1:
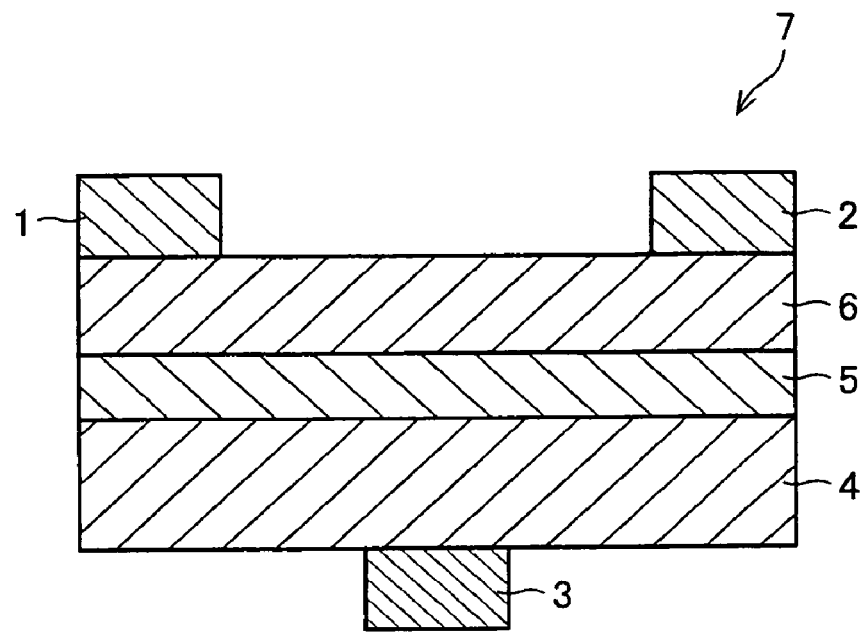
FIG. 1 is a cross-sectional view schematically illustrating a structure of an organic semiconductor device according to an embodiment of the present invention.

1: Source
2: Drain
3: Gate electrode contact
3a: Gate electrode
4: Silicon substrate (Gate electrode)
4a: Substrate
5: Dielectric layer
6: Organic semiconductor material (Organic semiconductor layer)
7: Organic semiconductor device
7A, 7B, 7C, 7D, 7E, 7F: Thin film transistor devices (Organic Semiconductor Devices)

DESCRIPTION OF EMBODIMENTS

The present invention will be described below in detail, but the scope of the present invention is not limited to the following description. Further, the present invention is not limited to the following examples, but may be appropriately modified within the gist of the present invention.

Embodiment 1

In order to obtain (a) a compound including: a BXBX skeleton further having an aromatic ring(s) located outside the BXBX skeleton, or (b) a compound including a BXBX skeleton in which a benzene ring is substituted with a heterocyclic ring, the inventors of the present invention diligently worked to find how to obtain a compound 1 by use of a reaction represented by the following Reaction Formula (1):

Chem. 21

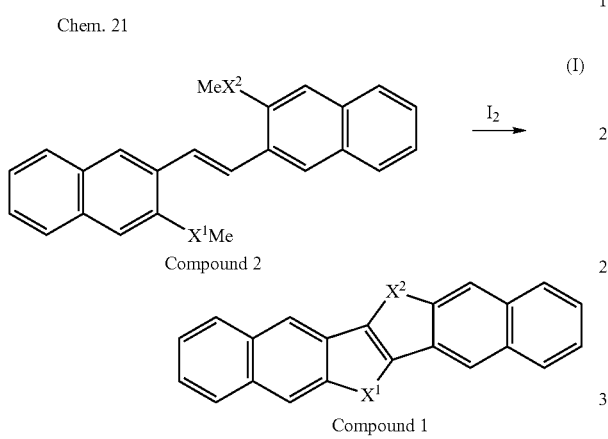

Compound 2

Compound 1

However, it was quite difficult to obtain a compound 2, which is a source material of the compound 1, and a compound 3, which is a source material for synthesizing the compound 2. The compound 3 is represented by the following General Formula (18):

Chem. 22

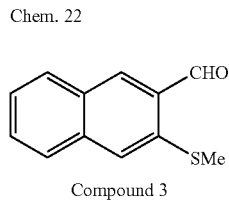

Compound 3

There is a compound 2a having a similar structure to the compound 2 and represented by General Formula (19):

Chem. 23

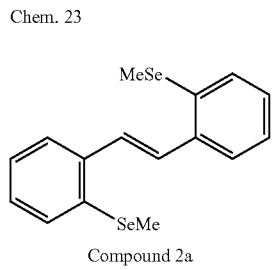

Compound 2a

The compound 2a can be obtained by reacting compounds 3a with each other, the compound 3a being represented by the following General Formula (20):

Chem. 24

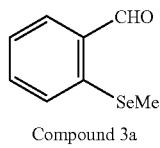

Compound 3a

The inventors synthesized the compound 3a by use of multi-stage reaction represented by the following Reaction Formula (II):

Chem. 25

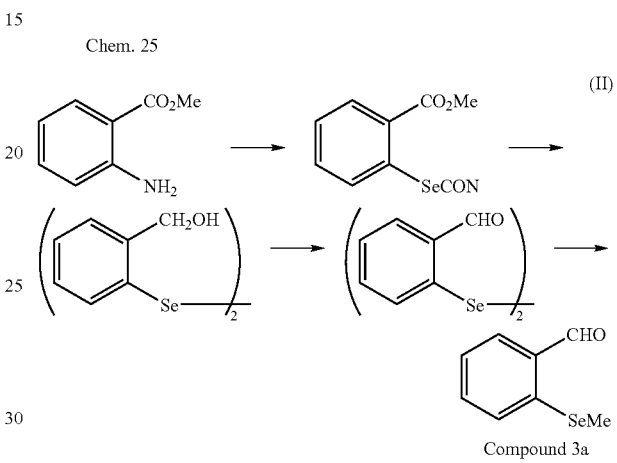

Compound 3a

In regard to Reaction Formula (II), the reason for using the multistage reaction is as follows. The inventors tried to find how to obtain the compound 3a, with the use of benzaldehyde as a material, by one-stage reaction represented by the following Reaction Formula (III).

Chem. 26

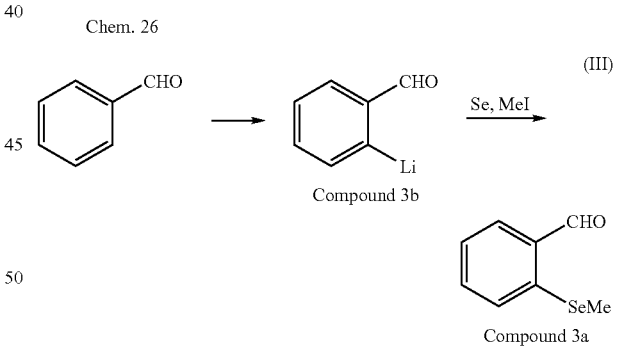

Compound 3b

Compound 3a

However, it was difficult to control generation of a compound 3b represented in Reaction Formula (III). Further, powdery selenium used for synthesizing the compound 3a did not efficiently react with the compound 3b, and it was difficult to find out an easy pathway for the synthesis.

In view of this, the inventors further diligently studied on this matter and found out stable conditions for a first-stage reaction, that is, for producing a reaction intermediate, i.e., an alkyl metal reagent, a reaction temperature, and an operating procedure used for metallation of an aromatic aldehyde by ortho-hydrogen substitution.

As a result of the studies, the inventors found out an efficient method for producing the compound 3. In addition, the inventors found that the compound 2 could be obtained by reacting the compounds 3 with each other, and further that the compound 1 could be obtained by cyclizing the compound 2. Moreover, the inventors generalized the reaction, and found out a method for producing various fused polycyclic aromatic compounds. Herewith, the present invention is accomplished.

More specifically, a production method of the present invention is to produce a compound represented by the following General Formula (7):

Chem. 28

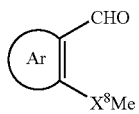

(7)

and the method includes the steps of (i) adding an alkyl metal reagent to a compound represented by General Formula (6):

Chem. 27

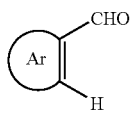

(6)

and (ii) after the step (i), adding a liquid reagent containing chalcogen atoms to the compound.

In both of the above formulae, $X^9$ is a chalcogen atom; and each Ar has a structure selected from the group consisting of the following chemical structures (a) through (c):

(a) a chemical structure having at least one benzene ring to fuse, in which a hydrogen atom may be substituted with an atom or a functional group selected from the group consisting of a halogen atom, an alkyl group, an alkenyl group, an alkynyl group, an aryl group, an alkyloxy group, and an alkylthio group;

(b) a chemical structure having at least one five-membered ring to fuse, represented by General Formula (8):

Chem. 29

(8)

and (c) a chemical structure represented by General Formula (9):

Chem. 30

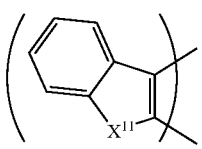

(9)

(where $X^{10}$ and $X^{11}$ are a chalcogen atom).

In the specification of the present invention, the "chalcogen atom" denotes oxygen, sulfur, selenium, or tellurium. Ar is a structure having at least one benzene ring to fuse, a structure having at least one fused selenophene, or a benzochalcogenophene ring.

The hydrogen atom in the benzene ring may be substituted with an atom or a functional group selected from the group consisting of a halogen atom, an alkyl group, an alkenyl group, an alkynyl group, an aryl group, an alkyloxy group, and an alkylthio group.

Examples of the halogen atom may be fluorine, chlorine, bromine, and iodine.

The alkyl group may be, for example, methyl, ethyl, propyl, butyl, or pentyl; the alkenyl group may be, for example, ethylene, propylene, butene, or pentene; and the alkynyl group may be, for example, acetylene, propine, butyne, or pentine. The number of carbons in the alkyl group, the alkenyl group, and the alkynyl group is not especially limited. Further, molecular structures of the alkyl group, the alkenyl group, and the alkynyl group may be straight, branched, or cyclic.

The aryl group may be, for example, phenyl, naphthyl, anthranil, furyl, thienyl, selenofuryl, or thienothienyl. It is preferable that the compound represented by General Formula (7) have such an aryl group. This allows the compound to be used as a material of a fused polycyclic aromatic compound that can realize an organic semiconductor device excellent in the electron field-effect mobility and the on/off current ratio.

The alkyloxy group may be, for example, methoxy, ethoxy, n-propoxy, isopropoxy, n-butoxy, or n-pentyloxy, but is not limited to these.

Further, the alkylthio group may be, for example, methylthio, ethylthio, n-propylthio, n-butylthio, or n-pentylthio, but is not limited to these.

A carbon atom in the alkyl group, the alkenyl group, the alkynyl group, the aryl group, the alkyloxy group, and the alkylthio group may be substituted with an oxygen atom and/or a sulfur atom. Further, at least one hydrogen atom, but not all of hydrogen atoms, included in the substituents may be substituted with a halogen atom, and its molecule structure is not especially limited. Furthermore, a part of the substituent may be substituted with the aryl group.

Further, it is preferable that each Ar independently have a chemical structure selected from the group consisting of the following chemical structures (A) through (F):

(A) a chemical structure represented by General Formula (10):

Chem. 31

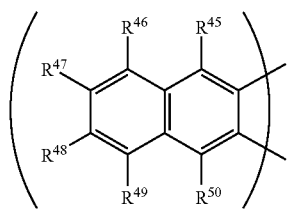

(10)

(B) a chemical structure represented by General Formula (11):

Chem. 32

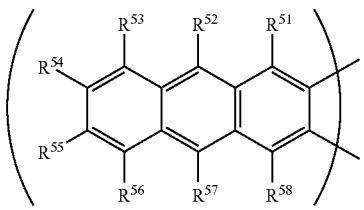

(11)

(C) a chemical structure represented by General Formula (12):

Chem. 33

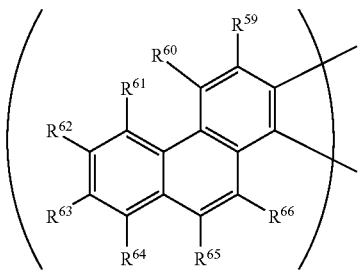

(12)

(D) a chemical structure represented by General Formula (13):

Chem. 34

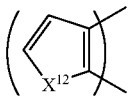

(13)

(E) a chemical structure represented by General Formula (14):

Chem. 35

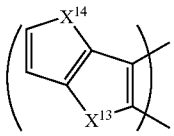

(14)

and (F) a chemical structure represented by General Formula (15):

Chem. 36

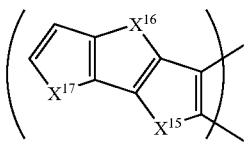

(15)

where $X^{12}$ through $X^{17}$ are independently a chalcogen atom; and $R^{45}$ through $R^{66}$ are independently at least one atom or functional group selected from the group consisting of a hydrogen atom, a halogen atom, an alkyl group, an alkenyl group, an alkynyl group, an aryl group, an alkyloxy group, and an alkylthio group.

The compound represented by General Formula (6) including Ar that has a chemical structure selected from the aforementioned groups is easily available. With the use of the compound, it is possible to readily carry out the aforementioned production method.

Examples of the alkyl metal reagent encompass butyllithium, methyllithium, phenyllithium, methylmagnesium chloride, butylmagnesium chloride, and the like. Among these alkyllithiums, the butyllithium is especially preferably used.

In the method of the present embodiment, it is preferable to add a basic compound as an additive, in addition to the alkyl metal reagent. The basic compound may be N,N,N'-trimethylethylenediamine, dimethylamine, diisopropylamine, morpholine, or the like.

It is preferable that not less than 2 mol but not more than 10 mol of the alkyl metal reagent be used per 1 mol of the compound represented by General Formula (6). After the alkyl metal reagent is added to the compound represented by General Formula (6), the alkyl metal reagent may be further added to a resultant reaction solution provided that the used amount of the alkyl metal reagent does not exceed the above range. The two-stage addition of the alkyl metal reagent enables more stable generation of an intermediate in which an ortho position in the compound represented by General Formula (6) is substituted with a metal such as lithium.

A temperature at which the compound represented by General Formula (6) reacts with the alkyl metal reagent is preferably not less than −30° C. but not more than 0° C., more preferably not less than −30° C. but not more than −20° C. The reaction temperature set in the above range can efficiently facilitate ortho-hydrogen abstraction in the compound represented by General Formula (6).

Further, a solvent for the reaction is preferably an ether solvent, e.g., tetrahydrofuran (THF), ether, dimethoxyethane, dioxane, or the like. It is preferable that these solvents be dried to restrain moisture intrusion.

The liquid reagent containing chalcogen atoms is a liquid type reagent that contains chalcogen atoms. Specifically, it is preferable to use dialkylchalcogenide such as dimethyl disulfide and dimethyl diselenide. These reagents can easily react with the compound represented by General Formula (6), with the result that the compound represented by General Formula (7) can be easily produced.

For the sake of efficient production of the compound represented by General Formula (7), the liquid reagent containing chalcogen atoms is used preferably in a range of an equivalent amount to a 10-time greater amount with respect to aldehyde.

The compound represented by General Formula (7) that is obtained by the foregoing production method may be purified. How to purify the compound represented by General Formula (7) is not especially limited, and a well-known purification method can be employed depending on properties of the compound. For example, the following method can be used. After the heating, the reaction solution in a reaction container is cooled down, and water is removed from the reaction solution by use of saturated sodium carbonate or the like. A resultant is then purified by column chromatography, sublimation purification, recrystallization, or the like.

Since a conventional technique requires multistage reaction processes, it is very difficult to obtain the compound represented by General Formula (7). In contrast, in the production method of the present embodiment, the compound represented by General Formula (7), which is highly purified, can be easily produced in such a simple manner that the alkyl metal reagent is added to the compound represented by General Formula (6), followed by adding the reagent containing chalcogen atoms thereto. Further, the compound represented by General Formula (7) includes a chalcogen atom, and can be used as a source material of a compound represented by General Formula (16). On this account, the production method of the present embodiment is very useful. The compound represented by General Formula (16) is a raw material for a compound represented by General Formula (17) that can be preferably used as an organic semiconductor material.

Explained below is a method for producing the compound represented by General Formula (16) by use of the compound represented by General Formula (7) as a raw material. The following method is just an example to obtain the compound represented by General Formula (16). The method for producing the compound represented by General Formula (16) is therefore not especially limited to the following method. As an exemplary method for producing the compound represented by General Formula (16), there is a production method by use of a reaction represented by the following Reaction Formula (IV).

Chem. 37

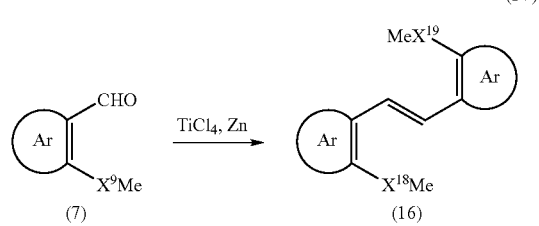

(IV)

First, a zinc reagent is mixed with a solvent in a reaction container such as a flask. In order to prevent moisture intrusion and the like, it is preferable that air in the reaction container be replaced with nitrogen or argon. As the zinc reagent, for example, powdery zinc or solid zinc can be used. The solvent may be, for example, an ether solvent such as tetrahydrofuran, dioxane, or dimethoxyethane. In order to prevent moisture contamination, it is preferable to use a dried solvent.

After a mixed solution of the zinc reagent and the solvent is cooled down, titanium tetrachloride is dropped into the solution. Not less than 0.1 mol but not more than 0.2 mol of the titanium tetrachloride can be dropped with respect to 1 mol of the zinc reagent. This range enables efficient coupling reaction of the compounds represented by General Formula (7) with each other. Further, it is preferable that, after the dropwise addition of titanium tetrachloride, a resultant mixed solution in the reaction container be heated to a temperature not less than 50° C. but not more than 200° C. Alternatively, the resultant mixed solution may be heated at a reflux temperature depending on a type of the solvent. A heating period may be appropriately changed depending on an amount of the raw material to be used. In a case where anhydrous tetrahydrofuran is used and the resultant reaction solution is to be heated at the reflux temperature, the heating period can be set not less than 1 hour but not more than 20 hours. Further, a magnetic stirrer or the like may be used for stirring the mixed solution in the reaction container.

After that, an obtained reactant in the reaction container is cooled down to a room temperature or a temperature lower than that, and the compound represented by General Formula (7) that is dissolved in the solvent is dropped into the reaction container. It is preferable that, after the compound has been dropped, a resultant mixed solution in the reaction container be heated again, or alternatively the resultant mixed solution may be heated at a reflux temperature depending on a type of the solvent. A heating period may be appropriately changed depending on an amount of a raw material to be used. In a case where anhydrous tetrahydrofuran is used and the resultant reaction solution is to be heated at the reflux temperature, the heating period can be set not less than 5 hours but not more than 30 hours.

After the heating is completed, an obtained compound represented by General Formula (16) may be purified. How to purify the compound represented by General Formula (16) is not especially limited, and a well-known purification method can be employed depending on properties of the obtained compound. For example, the following method can be used. That is, after the heating is completed, an obtained reaction solution in the reaction container is cooled down. Then, water is removed from the reaction solution by use of saturated sodium carbonate or the like. After that, the resultant is purified by column chromatography, sublimation purification, recrystallization, or the like. Instead of the titanium tetrachloride, titanium trichloride can be also used. Further, instead of the zinc reagent, lithium aluminum hydride can be also used.

Embodiment 2

Another embodiment of the present invention will be explained as follows. A production method of the present embodiment is to produce a compound represented by the following General Formula (17):

Chem. 35

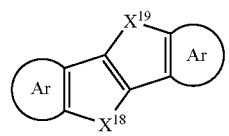

(17)

and the method of the present embodiment includes the steps of: (i) reacting compounds represented by General Formula (7) with each other so as to obtain a compound represented by General Formula (16):

Chem. 38

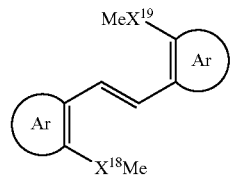

(16)

the compounds represented by General Formula (7) being obtained by the production method according to Embodiment 1; and (ii) after the step (i), reacting the obtained compound represented by General Formula (16) with iodine.

In both of the formulae, $X^{18}$ and $X^{19}$ are independently a chalcogen atom; each Ar independently has a structure selected from the group consisting of the following chemical structures (a) through (c):

(a) a chemical structure having at least one benzene ring to fuse, in which a hydrogen atom may be substituted with an atom or a functional group selected from the group consisting of a halogen atom, an alkyl group, an alkenyl group, an alkynyl group, an aryl group, an alkyloxy group, and an alkylthio group;

(b) a chemical structure having at least one five-membered ring to fuse, represented by General Formula (8):

Chem. 40

(8)

and (c) a chemical structure represented by General Formula (9):

Chem. 41

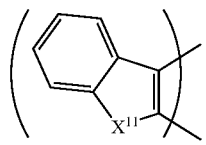

(9)

(where $X^{10}$ and $X^{11}$ are a chalcogen atom).

The halogen atom, alkyl group, alkenyl group, alkynyl group, aryl group, alkyloxy group, and alkylthio group are the same as those described in Embodiment 1.

Further, it is preferable that each Ar independently have a chemical structure selected from the group consisting of the following chemical structures (A) through (F):

(A) a chemical structure represented by General Formula (10):

Chem. 42

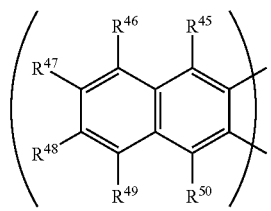

(10)

(B) a chemical structure represented by General Formula (11):

Chem. 43

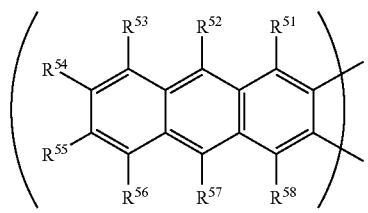

(11)

(C) a chemical structure represented by General Formula (12):

Chem. 44

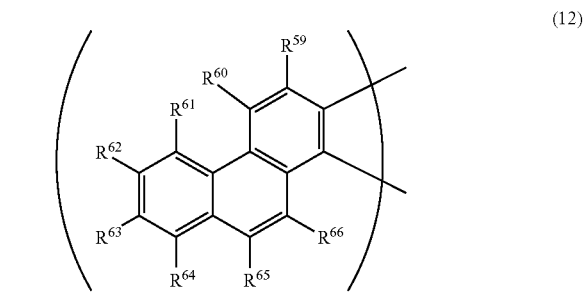

(12)

(D) a chemical structure represented by General Formula (13):

Chem. 45

(13)

(E) a chemical structure represented by General Formula (14):

Chem. 46

(14)

and (F) a chemical structure represented by General Formula (15):

Chem. 47

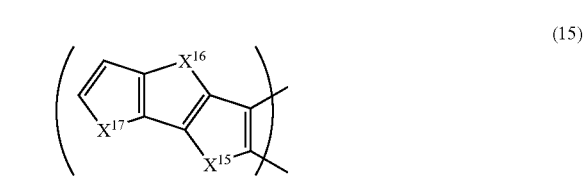

(15)

(where $X^{12}$ through $X^{17}$ are independently a chalcogen atom; and $R^{45}$ through $R^{66}$ are independently at least one atom or functional group selected from the group consisting of a hydrogen atom, a halogen atom, an alkyl group, an alkenyl group, an alkynyl group, an aryl group, an alkyloxy group, and an alkylthio group).

If Ar has a chemical structure selected from the aforementioned group, the compound represent by General Formula (6) can be made from the compound represented by General Formula (16), which is easily available. With the use of the compound represented by General Formula (16), it is possible to readily carry out the aforementioned production method.

It is not necessary that the each Ar included in the compound represented by General Formula (16) for use in the above production method have the same chemical structure, and the each Ar may have a different chemical structure. In a case where the each Ar has a different chemical structure, General Formula (17) can be asymmetrical, which allows a broader molecular design. Further, in a case where the each Ar has the same chemical structure, an obtained compound represented by General Formula (17) will be a single substance, thereby facilitating purification and reducing a production cost.

The iodine for use in the production method is not especially limited, and may be one that is commercially available. It is preferable that not less than 2 mol but not more than 100 mol of the iodine be used with respect to 1 mol of the compound represented by General Formula (16). The iodine used within the range enables efficient generation of the compound represented by General Formula (17).

A solvent used in the reaction of the compound represented by General Formula (16) with the iodine can be, for example, a halogenated hydrocarbon solvent such as chloroform, methylene chloride, carbon tetrachloride, or dichloroethane.

A reaction temperature for the reaction should be not less than 30° C. but not more than 200° C. In a case where chloroform is used as a solvent, the reaction may be carried out at a reflux temperature. In this case, a reaction period can be not less than 1 hour but not more than 100 hours.

After the reaction is completed, an obtained compound represented by General Formula (17) may be purified. How to purify the compound represented by General Formula (17) is not especially limited, and a well-known method can be employed depending on properties of the compound represented by General Formula (17). For example, the following method can be used. After the heating, the reaction solution in a reaction container is cooled down, and water is removed from the reaction solution by use of saturated sodium carbonate or the like. A resultant is then purified by column chromatography, sublimation purification, recrystallization, or the like.

The production method of the present embodiment makes it possible to produce the compound represented by General Formula (17) according to the present invention, at a high yield with a few reaction processes. In addition, since the production method is not carried out in multiple stages, the obtained compound represented by General Formula (17) is hardly contaminated with impurities. Further, the compound is (a) a compound including: a BXBX skeleton further having an aromatic ring(s) located outside the BXBX skeleton, or (b) a compound including a BXBX skeleton in which a benzene ring is substituted with a heterocyclic ring. In other words, the compound has a large number of the fused rings, and has electrical, electronic, and photoelectric properties. The compound is very useful in that the compound can be used as a highly soluble semiconductor material. Besides, since the number of the fused rings contained in the compound is not much, the compound is highly soluble with respect to a solvent and is highly stable in the atmosphere. On this account, the compound can be preferably used as an organic semiconductor material.

In this way, the above production method can produce a compound represented by General Formula (1) including: a benzodichalcogenophenobenzodichalcogenophene skeleton having benzene rings, at least one of which is fused to another benzene ring(s), where $X^1$ and $X^2$ is independently a chalcogen atom, and a hydrogen atom in the benzene ring(s) may be substituted with an atom or a functional group selected from the group consisting of a halogen atom, an alkyl group, an alkenyl group, an alkynyl group, an aryl group, an alkyloxy group, and an alkylthio group. In a case where both $X^1$ and $X^2$ are sulfur atoms, the compound represented by General Formula (1) is a compound represented by General Formula (2) where $R^1$ through $R^{12}$ are independently at least one atom or functional group selected from the group consisting of a hydrogen atom, a halogen atom, an alkyl group, an alkenyl group, and alkynyl group, an aryl group, an alkyloxy group, and an alkylthio group. Further, it is possible to produce a compound represented by General Formula (5) where $X^3$ through $X^8$ is independently a chalcogen atom.

In a case where the production method is carried out especially with the use of the following compounds: 1,2-bis(3-methylthio-2-naphthyl)ethylene, 1,2-bis(3-methylseleno-2-naphthyl)ethylene, 1,2-bis(3-methylthio-2-anthranil)ethylene, 1,2-bis(3-methylseleno-2-anthranil)ethylene, 1,2-bis(3-methylthio-2-phenanthro)ethylene, 1,2-bis(3-methylseleno-2-phenanthro)ethylene, and 1,2-bis(3-methylthio-2-thieno[3,2-[b]thiopheno])ethylene, the following novel compounds respectively can be obtained: dinaphtho[2,3-b: 2',3'-f]thieno[3,2-b]thiophene, dinaphtho [2,3-b: 2', 3'-f]selenopheno[3,2-b]selenophene, dianthra[2,3-b:2',3'-f]thieno[3,2-b]thiophene, dianthra[2,3-b: 2',3'-f]selenopheno[3,2-b]selenophene, diphenanthro[2,3-b: 2',3'-f]thieno[3,2-b]thiophene, diphenanthro[2,3-b:2',3'-f]selenopheno[3,2-b]selenophene, and hexathienoacene.

These compounds are either (a) a compound including: a BXBX skeleton further having an aromatic ring(s) located outside the BXBX skeleton or (b) a novel fused polycyclic aromatic compound including a BXBX skeleton in which a benzene ring is substituted with a heterocyclic ring. Such novel fused polycyclic aromatic compounds having more fused rings than the BXBX strengthens intermolecular interaction due to greater π electron orbits. When these compounds are used as a material of the organic semiconductor device, it is possible to improve the electron field-effect mobility. On this account, the compounds can be used as a very useful material to develop a new organic semiconductor device.

Embodiment 3

The following explains still another embodiment of the present invention with reference to FIG. 1. The present embodiment deals with an organic semiconductor device employing the above-described organic semiconductor material as its organic semiconductor material. FIG. 1 is a schematic cross sectional view of a structure of the organic semiconductor device (thin film transistor device), illustrating one embodiment of the present invention.

The organic semiconductor device in accordance with the present embodiment employs, as the organic semiconductor material, at least one compound selected from the group consisting of (i) the novel fused polycyclic aromatic compounds and (ii) the compounds represented by the general formula (17) obtained by the production method described in Embodiment 2. The organic semiconductor material may include either only one of the compounds or several types of the compounds together, as the fused polycyclic aromatic compound(s). In a case where the organic semiconductor material includes only one of the fused polycyclic aromatic compounds, it is possible to easily deposit the organic semiconductor material in a step (described later) of depositing the organic semiconductor material. In a case where the organic semiconductor material employs several types of the fused polycyclic aromatic compounds together, it is possible to adjust a physical property of the organic semiconductor material by appropriately selecting the fused polycyclic aromatic compounds for use.

In FIG. 1, an organic semiconductor device 7 of the present invention includes a gate electrode contact 3 on a surface of a substrate 4, which functions as a gate electrode. A dielectric layer 5 is provided on another surface of the substrate 4, which surface is opposite to the surface of the substrate 4 on which the gate electrode contact 3 is provided. Further, an organic semiconductor material 6 is provided on the dielectric layer 5. A source 1, a drain 2, and a contact channel between the source 1 and the drain 2 are provided on the organic semiconductor material 6.

The substrate 4 is not limited to either p-type or n-type, but is preferably n-doped in order to act as a gate electrode. Further, regarding a material from which the substrate 4 is made, the substrate 4 may be: a ceramic substrate (glass, quartz, aluminum oxide, sapphire, silicon nitride, or silicon carbide, for example); a semiconductor substrate (silicon, germanium, gallium arsenide, gallium phosphide, or gallium nitrogen, for example); a polyester (polyethylene terephthalate, or polynaphthalene terephthalate, for example); a resin substrate (polyethylene, polypropylene, polyvinyl alcohol, an ethylene-vinylalcohol copolymer, cyclic polyolefin, polyimide, polyamide, or polystyrene, for example); paper; and nonwoven fabric. Among these, silicon is particularly suitable for the material of the substrate 4.

Metal suitable for the gate electrode contact 3 may be, but not limited to, gold, platinum, silver, copper, aluminum, nickel, titanium, chrome, magnesium-silver, an organic conductive compound, or calcium. For the sake of easy handling, the gate electrode contact 3 is preferably made from gold, or silver. In a case where the substrate 4 is made from silicon, it is possible for the dielectric layer 5 to be made from silicon dioxide.

It is preferable to carry out thermal oxidation as a method of forming the dielectric layer 5 on the substrate 4. Further, a method of forming the contact channel between the source 1 and the drain 2 may be, but not limited to, an electron beam lithography, a photolithographic method, a shadow mask method, or a silkscreen method. The contact channel is preferably formed by the shadow mask method, the electron beam lithography, or the photolithographic method.

A method of depositing the organic semiconductor material 6 on the dielectric layer 5 may be, but not limited to, a dry film forming method (a vacuum deposition method, a CVD method, a sputtering method, or a laser deposition method, for example), or a wet film forming method in which, after a solution or a dispersion liquid is applied to a substrate, a solvent or a dispersion medium is removed so as to form a thin film, for example. The vacuum deposition method is preferably used to deposit the organic semiconductor material 6 on the dielectric layer 5. In a case where the vacuum deposition method is used, a pressure is preferably not more than $10^{-1}$ Pa, more preferably, not more than $10^{-3}$ Pa.

In a case where the organic semiconductor material 6 is deposited on the dielectric layer 5 made from silicon dioxide, it is preferable to coat a surface of the dielectric layer 5 in advance with octyltrichlorosilane, hexamethyldisilazane, or the like, each of which is a silane coupling agent. Further, a temperature of the substrate 4 is usually in a range of approximately a room temperature to 140° C., preferably in a range of approximately 40° C. to 120° C., more preferably, not less than 60° C. but not more than 100° C. With the coating described above, and/or with the substrate 4 being in the temperature range described above, it is possible to improve the organic semiconductor device 7 in electron field-effect mobility and on/off current ratio.

Here, since the organic semiconductor material 6 usually has a strong tendency to become p-type (hole transport type), a lot of excellent p-type organic semiconductor materials have been developed. On the other hand, types of n-type (electron transport type) materials are limited, and qualities of the n-type materials are usually lower than those of the p-type materials. Therefore, there has been a great demand for development of the n-type organic semiconductor materials and a method of manufacturing the n-type organic semiconductor materials.

In the development of the n-type organic semiconductor materials, there has been an effective method in which dipole inversion of the organic semiconductor material from p-type to n-type is conducted by introducing an electron-attracting substituent into a p-type organic semiconductor material that exhibits an advantageous property. In order to conduct such dipole inversion, a substituent group including a plurality of cyanos, a plurality of fluorines, or the like, has been suitably used. In other words, a person skilled in the art can convert an organic semiconductor material, which is generally the p-type, into the n-type, if necessary.

The organic semiconductor device 7 of the present invention, having the arrangement illustrated in FIG. 1, may be used as a diode, a thin film transistor, a memory, a photodiode, a light-emitting diode, a light-emitting transistor, a gas sensor, a biosensor, a blood sensor, an immune sensor, an artificial retina, a taste sensor, or the like. It is preferable that the organic semiconductor device 7 function as the thin film transistor, or a light-emitting device.

The thin film transistor can be preferably used as a transistor for switching pixels constituting a display, a signal driver circuit element, a memory circuit element, a signal processing circuit element, or the like.

A thickness of the thin film transistor can be determined in accordance with a structure or a size of a device, as appropriate. The thickness is generally not less than 10 nm but not more than 1000 nm, for example. However, the thickness is not limited to this. A "thin film" is preferably as thin as possible. The thin film suitable for use in the organic semiconductor device preferably has a thickness of not less than 1 nm but not more than 1 μm, more preferably not less than 5 nm but not more than 500 nm, further more preferably not less than 10 nm but not more than 500 nm.

Examples of a display encompass a liquid crystal display, a dispersed liquid crystal display, an electrophoretic display, a particle rotation display element, an electrochromic display, an organic electroluminescence display, electronic paper, and the like.

Further, the organic semiconductor device of the present invention is preferably a light-emitting device including an organic carrier transporting layer and/or a light-emitting layer. For example, the organic semiconductor device may be either a light-emitting device including only the organic carrier transporting layer, or a light-emitting device including both the organic carrier transporting layer and the light-emitting layer.

When the organic carrier transporting layer is provided, carriers freely move in the transporting layer. This allows easy formation of an electrode or the like in manufacturing the semiconductor device. Furthermore, the presence of the light-emitting layer can provide a field for a recombination between holes injected from an anode and electrons injected from a cathode while a voltage is being applied. Moreover, when both the organic carrier transporting layer and the light-emitting layer are provided, carriers can freely move in the transporting layer and transport, to the light-emitting layer, holes injected from an anode and electrons injected from a cathode while a voltage is being applied. This can cause the organic semiconductor device to emit light.

The organic carrier transporting layer is a layer for transporting carriers to the light-emitting layer. There are two types of the organic carrier transporting layer, that is, a hole transporting layer and an electron transporting layer. The hole transporting layer has a function of transporting, to the light-emitting layer, the holes injected from the anode. The electron transporting layer has a function of transporting, to the light-emitting layer, the electrons injected from the cathode.

Further, the light-emitting layer is a semiconductor layer including a light-emitting material. While a voltage is being applied, it is possible to inject, into the semiconductor layer, the holes from the anode and the electrons from the cathode, thereby providing a field for recombining the holes with the electrons. Examples of the light-emitting material encompass the following various low molecular light-emitting materials and various polymeric light-emitting materials. At least one of the light-emitting materials can be used.

The low molecular light-emitting material may be a publicly-known conventional compound such as a benzene compound (distyrylbenzene (DSB) or diamino-distyrylbenzene (DADSB), for example); a naphthalene compound (naphthalene or nile red, for example); or a phenanthrene compound (phenanthrene, for example).

Further, the polymeric light-emitting material may be a publicly-known conventional compound such as a polyacetylene compound (trans-polyacetylene, cis-polyacetylene, poly(diphenylacetylene) (PDPA), or poly(alkylphenylacetylene) (PAPA), for example), or poly(para-phenylenevinylene) (PPV), for example.

Moreover, when the organic carrier transporting layer includes the light-emitting material described above, it is possible to manufacture a light-emitting device not including a light-emitting layer but including the organic carrier transporting layer.

That is, in a case where a hole transporting layer includes the light-emitting material, an obtained light-emitting device includes a hole transporting light-emitting layer and an electron transporting layer. Further, in a case where an electron transporting layer includes the light-emitting material, an obtained light-emitting device includes an electron transporting light-emitting layer and a hole transporting layer. In such cases, each of (i) a region in the vicinity of an interface between the hole transporting light-emitting layer and the electron transporting layer, and (ii) a region in the vicinity of an interface between the electron transporting light-emitting layer and the hole transporting layer functions as the light-emitting layer.

Furthermore, an organic EL element is a concrete example of the light-emitting device of the present invention that includes the organic carrier transporting layer and/or the light-emitting layer. Other than the organic EL element employing the organic semiconductor material of the present invention, there have been a well-known organic EL element and a well-known method of manufacturing the organic EL element, for example, as disclosed in Japanese Patent Application Publication Tokukai No. 2006-199909 A. Specifically, the above organic EL element can include: a substrate; an anode layer provided on the substrate; a semiconductor layer including the organic semiconductor material of the present invention, which layer is provided on an anode; a cathode layer provided on the semiconductor layer; and a protection film that is provided so as to cover each of the layers.

The semiconductor layer includes an organic carrier transporting layer and/or a light-emitting layer. Further, the organic carrier transporting layer includes two layers, that is, a hole transporting layer and an electron transporting layer. In a case where the semiconductor layer includes both the organic carrier transporting layer and the light-emitting layer, the semiconductor layer is formed such that the hole transporting layer, the light-emitting layer, and the electron transporting layer are provided on the anode in this order. The hole transporting layer has a function of transporting, to the light-emitting layer, holes injected from the anode, and the electron transporting layer has a function of transporting, to the light-emitting layer, electrons injected from the cathode.

With the arrangement, when a current is passed (a voltage is applied) between the anode and the cathode, the holes move inside the hole transporting layer, and the electrons move inside the electron transporting layer. Then, the holes and the electrons are recombined with each other in the light-emitting layer. In the light-emitting layer, energy generated in the recombination generates exciton. The exciton generates energy (fluorescence or phosphorescence, for example) when returning to a ground state, thereby emitting light.

Further, the semiconductor layer may not include the light-emitting layer but include the organic carrier transporting layer. With the arrangement, it is possible to use the hole transporting light-emitting layer or the electron transporting light-emitting layer, as the organic carrier transporting layer. In this case, each of (i) the region in the vicinity of the interface between the hole transporting light-emitting layer and the electron transporting layer, and (ii) the region in the vicinity of the interface between the electron transporting light-emitting layer and the hole transporting layer functions as the light-emitting layer. In a case of using the hole transporting light-emitting layer, the holes injected from the anode into the hole transporting light-emitting layer are trapped by the electron transporting layer. Further, in a case of using the electron transporting light-emitting layer, the electrons injected from the cathode into the electron transporting light-emitting layer is trapped in the electron transporting light-emitting layer. Both of the cases have an advantage in improvement of efficiency of the recombination between the holes and the electrons.

Furthermore, the semiconductor layer may not include the organic carrier transporting layer but include the light-emitting layer. With the arrangement, it is possible to use a light-emitting layer including the organic semiconductor material of the present invention and the light-emitting material described above.

Here, the substrate will be a supporting member of the organic EL element. Each of the layers described above is provided on the substrate. A material having transparency and a high optical property can be used as a constituent material of the substrate.

Examples of such a material encompass: various resin materials such as polyethylene terephthalate, polyethylene naphthalate, polypropylene, a cyclo-olefin polymer, polyamide, polyethersulphone, polymethyl methacrylate, polycarbonate, and polyarylate; and various glass materials. At least one of these materials can be used.

A thickness of the substrate is not particularly limited. However, the thickness is preferably not less than 0.1 mm but not more than 30 mm, more preferably not less than 0.1 mm but not more than 10 mm.

The anode is an electrode for injecting holes into the hole transporting layer. Further, in order to cause the light emitted from the light-emitting layer to be visible, the anode is substantially transparent (colorless-transparent, colored-transparent, or translucent, for example). Examples of a material of such an anode encompass: an oxide (ITO (Indium Tin Oxide), $SnO_2$, Sb-containing $SnO_2$, or Al-containing ZnO, for example); Au; Pt; Ag; Cu; and an alloy containing these. At least one of these materials can be used.

The anode is not particularly limited in terms of its thickness. However, the thickness is preferably not less than 10 nm but not more than 200 nm, more preferably not less than 50 nm but not more than 150 nm. An excessively thin anode would not sufficiently function as an anode. On the other hand, an excessively thick anode would cause a significant decrease in its light transmission to an impractical level, depending on which material the anode is made from.

Meanwhile, the cathode is an electrode for injecting electrons into the electron transporting layer. Examples of a material of such a cathode encompass: Li; Mg; Ca; Sr; La; Ce; Er; Eu; Sc; Y; Yb; Ag; Cu; Al; Cs; Rb; and an alloy of these. At least one of these materials can be used.

A thickness of the cathode is preferably not less than 1 nm but not more than 1 μm, more preferably not less than 100 nm but not more than 400 nm. If the cathode is too thin, there is a risk that a function as a cathode is not sufficiently exhibited. On the other hand, if the cathode is too thick, there is another risk that a light-emitting efficiency of the organic EL element decreases.

The organic semiconductor material of the present invention can be provided as any of the hole transporting layer, the light-emitting layer, and the electron transporting layer of the semiconductor layer. Therefore, the light-emitting device of the present invention, including the organic carrier transporting layer and/or the light-emitting layer, includes: a device in which the organic semiconductor material is provided as one of the layers in the semiconductor layer; a device in which the organic semiconductor material is provided as a plurality of the layers in the semiconductor layer; and a device in which the organic semiconductor material is provided as all of the layers in the semiconductor layer.

In order to provide the organic semiconductor material of the present invention as any of the layers of the semiconductor layer described above, it is possible to use the vacuum deposition method. However, it is preferable to use the wet film formation method described above to provide the organic semiconductor material as each of the layers. With the use of the wet film formation method, it is possible to easily manufacture a lightweight, flexible, and large-area organic EL element at low cost.

Further, a layer for a purpose may be provided between any of the layers included in the organic EL element. For example, between the hole transporting layer and the anode, a hole injection layer may be provided for improving injection efficiency of the holes injected from the anode. Further, between the electron transporting layer and the cathode, an electron injection layer may be provided for improving injection efficiency of the electrons injected from the cathode. As such, in a case where the hole injection layer and the electron injection layer are provided in the organic EL element, it is possible to use the organic semiconductor material of the present invention as a constituent material of the hole injection layer and the electron injection layer.

It is preferable that each of the layers constituting the organic EL element be covered with the protection film. The protection film has a function of intercepting oxygen or moisture by sealing each of the layers constituting the organic EL element airtightly. By providing the protection layer, it is possible to obtain effects such as improvement in reliability of the organic EL element and prevention of qualitative change and deterioration of the organic EL element.

Examples of a constituent material of the protection layer encompass: Al; Au; Cr; Nb; Ta; Ti; an alloy of these; silicon oxide; and various resin materials. In a case of using a conductive material as the constituent material of the protection layer, it is preferable to provide an insulating film between the protection film and each of the layers in order to prevent a short-circuit, if necessary.

If the organic semiconductor device exhibits high values of the electron field-effect mobility (μ) and the on/off current ratio ($I_{on}/I_{off}$), it is considered that the organic semiconductor device can provide high performance as an organic electron field-effect transistor (FET element). Generally, a high-performance organic semiconductor device exhibits an electron field-effect mobility (μ) of not less than $1 \times 10^{-3}$ or an on/off current ratio ($I_{on}/I_{off}$) equal to $1 \times 10^{-3}$. However, the organic semiconductor device of the present embodiment employs the fused polycyclic aromatic compound described above, so that it is possible to realize an organic semiconductor device, which exhibits a high electron field-effect mobility and a high on/off current ratio.

Specifically, the organic semiconductor device of the present invention preferably has an electron field-effect mobility of not less than 1.0 cm²/Vs. This makes it possible to provide an organic semiconductor device that is advantageously excellent in light emission efficiency, low-voltage drive, and switching speed.

Further, the organic semiconductor device of the present invention preferably has an on/off current ratio of not less than $10^5$. By setting the on/off current ratio to be the above value, a ratio of an on-current to an off-current becomes large, which causes a current to be large in an on-state where the largest current flows between the source and the drain. Thereby, it becomes possible to provide a high performance organic semiconductor device.

The electron field-effect mobility is calculated by the following formula:

$$\mu = 2L \cdot I_D / C_0 \cdot W(V_g - V_{th})^2$$

where μ is an electron field-effect mobility [cm²V⁻¹S⁻¹], L is a channel length [cm], W is a channel width [cm], $C_0$ is a gate electric capacity, $V_g$ is a gate voltage, $V_{th}$ is a threshold voltage, and $I_D$ is an amount of a current at $V_g$. The threshold voltage $V_{th}$ is found in such a manner that (i) a linear approximate straight line of a plot of "$V_g - Id^{1/2}$ ($I_d^{1/2}$ is a square root of a current value)" is found, and (ii) based on the linear approximate straight line thus found, $V_g$ is found as a threshold voltage in a case of $I_d = 0$.

Furthermore, the on/off current ratio is calculated as described below. That is, an off-state is defined as a state where a current ($I_d$) between the source and the drain is at a minimum due to application of zero or sufficiently low gate voltage ($V_g$). An on-state is defined as a state where the current between the source and the drain is largest due to application of the gate voltage. The on/off ratio is calculated as a ratio of the current ($I_d$) between the source and the drain in the on-state to the current ($I_d$) between the source and the drain in the off-state.

As described above, the organic semiconductor device is a considerably-high performance device, so that it is possible to use the organic semiconductor device excellently as the light-emitting device including the organic carrier transporting layer or the light-emitting layer. Moreover, not only does the organic semiconductor device of the present invention have a high electron field-effect mobility, but, even in the atmosphere, the organic semiconductor device also can be in operation without a significant decrease in its performance.

The following explains about the organic semiconductor device (thin film transistor device) of the present invention more specifically. The thin film transistor device of the present invention is also called "electron filed-effect transistor (hereinafter, often referred to as FET)". The thin film transistor device includes two electrodes (a source electrode and a drain electrode) that are in contact with a semiconductor, and controls a current between the electrodes by a voltage that is applied to another electrode called "gate electrode".

Generally, the thin film transistor device has a structure in which the gate electrode is insulated by an insulating film (Metal-Insulator-Semiconductor; MIS structure). In a case where a metal oxide film is used as the insulating film, the structure is called "MOS structure". In addition to the structures, a structure in which the gate electrode is provided via a Schottky barrier, that is, an MES structure, is also used. However, in a case of the FET employing an organic semiconductor material, the MIS structure is usually used.

The following further explains one embodiment of the thin film transistor device of the preset invention with reference to drawings. However, the present invention is not limited to those devices explained below.

Figure 2:
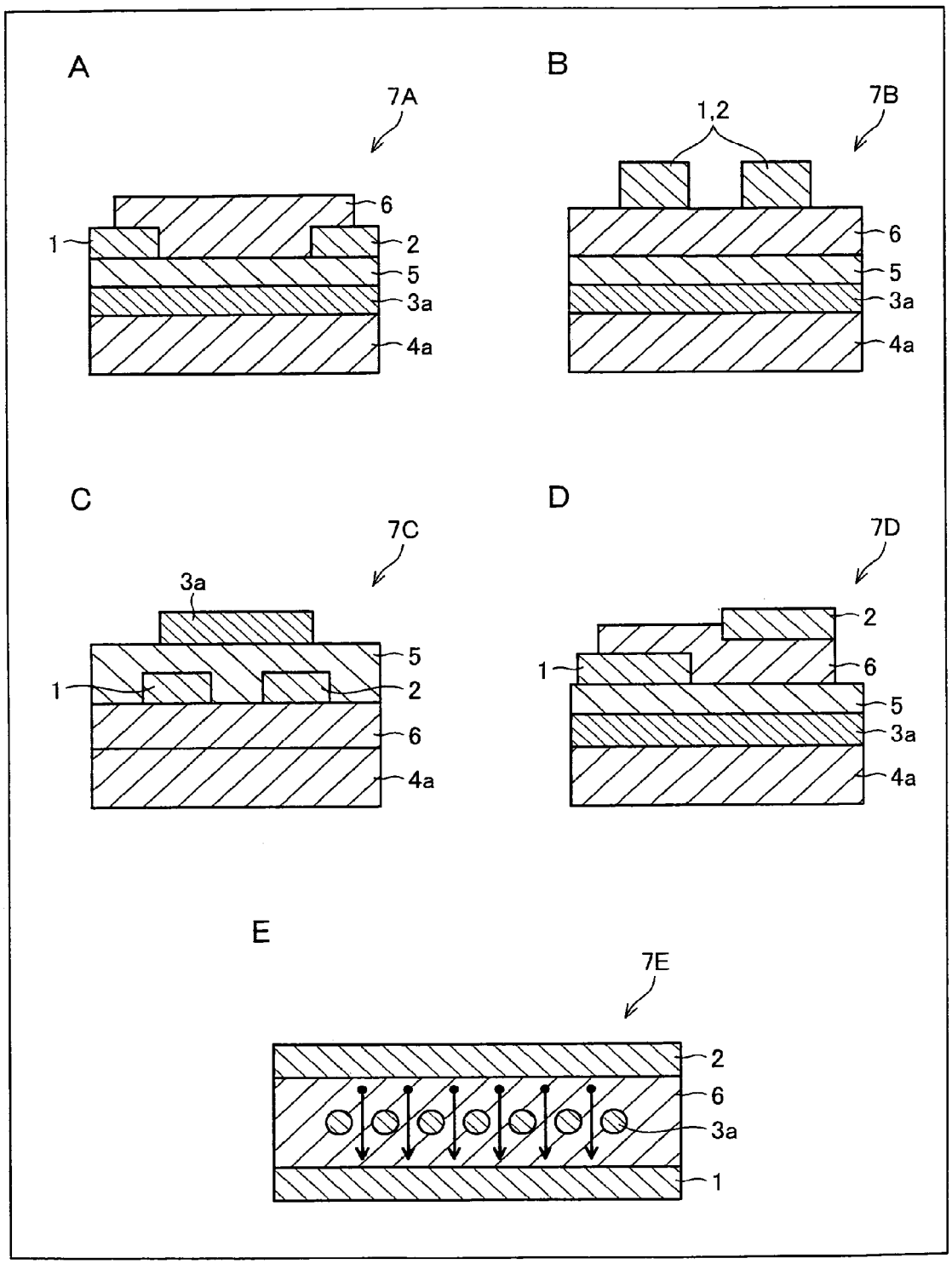
FIG. 2 is cross sectional views schematically illustrating structures of organic semiconductor devices according to embodiments of the present invention.

FIG. 2 illustrates several exemplary embodiments of the thin film transistor device of the present invention (thin film transistor devices 7A through 7E). In each of the exemplary embodiments, 1 is a source (source electrode), 2 is a drain (drain electrode), 3a is a gate electrode, 4a is a substrate, 5 is a dielectric layer, and 6 is an organic semiconductor material. A position of each of the layers and electrodes can be selected as appropriate in accordance with usage of the element. FETs illustrated in A through D in FIG. 2 are called "lateral FET" because a current flows in a direction parallel to the substrate 4a. A structure in A is called "bottom-contact structure", and B illustrates an FET called "top-contact structure". The thin film transistor device explained in FIG. 1 corresponds to B in FIG. 2, that is, the top-contact structure. In FIG. 2, the "gate electrode 3a" is clearly illustrated, but the "gate electrode contact 3" illustrated in FIG. 1 is omitted. The "gate electrode contact 3" can be provided anywhere in contact with the gate electrode 3a, provided that the source 1 and the drain 2 will not be electrically short-circuited with each other. Further, as illustrated in A, B, and D of FIG. 2, in a case of an arrangement in which the gate electrode 3a is in contact with the substrate 4a and the substrate 4a is a conductive substrate, the "gate electrode contact 3" can be provided anywhere that is in contact with the substrate 4a.

C is a structure which is often used in manufacture of an organic single-crystal FET. In the structure, the source 1, the drain 2, and the dielectric layer 5 (insulating layer) are provided on the organic semiconductor material 6, and further, the gate electrode 3a is provided thereon. D illustrates a thin layer transistor 7D having a structure called "top and bottom contact type transistor".

E is a view schematically illustrating an FET having a vertical structure, that is, a static induction transistor (SIT). In the SIT, a flow of the current spreads in a planar manner so that a large amount of carriers can move at one time. Further, the source 1 and the drain 2 are provided to face each other in a vertical direction so that it is possible to reduce a distance between the electrodes. This enables a quick response. Therefore, the SIT can be suitably used for the purpose of flowing a large current, or performing a high-speed switching, for example. In E illustrated in FIG. 2, the substrate 4a is not illustrated. However, substrates are usually provided on outer surfaces of the source 1 and the drain 2 in E illustrated in FIG. 2.

The following explains each constituent in each of the exemplary embodiments.

The substrate 4 and the substrate 4a should be able to keep each of the layers provided thereon so that each of the layers is not separated from the substrates. For this reason, the substrates may be made from, for example: an insulating material (a resin substrate, a film, paper, glass, quartz, or ceramic, for example); a product manufactured in such a manner that an insulating layer is formed on a conductive substrate (metal or platinum, for example) by a coating method or the like; materials made from various combinations (a combination of a resin and an inorganic material, for example); or the like. Examples of the resin film that can be used as a constituent of each of the substrates encompass: polyethylene terephthalate; polyethylene naphthalate; polyethersulphone; polyamide; polyimide; polycarbonate; cellulose triacetate; and polyetherimide. With the use of a resin film or paper, it is possible to obtain a flexible thin film transistor device. This makes it possible to obtain the device that is flexible, light in weight, and is improved in practicality. A thickness of each of the substrates is usually in a range of 1 μm to 10 mm, preferably, in a range of 5 μm to 5 mm.

The source 1, the drain 2, and the gate electrode 3a are made from a conductive material. Examples of the conductive material encompass: metals (platinum, gold, silver, aluminum, chrome, tungsten, tantalum, nickel, cobalt, copper, iron, lead, tin, titanium, indium, palladium, molybdenum, magnesium, calcium, barium, lithium, potassium, and sodium, for example) and an alloy of these; conductive oxides ($InO_2$, $ZnO_2$, $SnO_2$, and ITO, for example); conductive polymeric compounds (polyaniline, polypyrrole, polythiophene, polyacetylene, polypara-phenylene, vinylene, or polydiacetylene, for example); semiconductors (silicon, germanium, and gallium arsenide, for example); and carbon materials (carbon black, fullerene, carbon nanotube, and graphite, for example). Further, it is possible that a conductive polymeric compound or a semiconductor has been doped in advance. Examples of a dopant in the doping encompass: inorganic acids (hydrochloric acid and sulfuric acid, for example); organic acids including an acid functional group, such as sulfonic acid; Lewis acids ($PF_5$, $AsF_5$, and $FeCl_3$, for example); halogen atoms (iodine, for example); and metal atoms (lithium, sodium, and potassium, for example). Boron, phosphorus, arsenic, or the like has been often used as a dopant for an inorganic semiconductor such as silicon, as well. Furthermore, the dopant also includes a conductive composite material made in such a manner that carbon black or metal particles are dispersed in the dopant described above.

Moreover, a distance (channel length) between the source 1 and the drain 2 (drain electrode) is an important factor for determining a property of the element. The channel length is usually in a range of 300 μm to 0.5 μm, preferably in a range of 100 μm to 2 μm. By reducing the channel length, it becomes possible to have a larger amount of the current. In this case, however, a leak current or the like occurs. Therefore, it is necessary to determine an appropriate length of the channel. A width (channel width) between the source 1 and the drain 2 is usually in a range of 5000 μm to 10 μm, preferably in a range of 3000 μm to 100 μm. This channel width can be set longer than the above values by forming, for example, a structure of an electrode to be a comb-shaped structure. The channel width may be set appropriately in accordance with a necessary amount of the current, a structure of the element, or the like.

The following explains each structure (shape) of the source 1 and the drain 2. The source 1 and the drain 2 may have either the same structure, or structures different from each other. In a case where the thin film transistor device has the bottom-contact structure, generally, it is preferable to (i) manufacture each of the electrodes by a lithographic method, and (ii) form each of the electrodes into a rectangular solid shape. Lengths of the source 1 and the drain 2 (electrodes) may be the same as the channel width described above. A width (a length between the electrodes) between the source 1 and the drain 2 is not particularly limited. However, in order to reduce an area of the element to an extent that an electrical property can be stabilized, the width is preferably short. A width of each of the electrodes is usually in a range of 5000 μm to 10 μm, preferably in a range of 3000 μm to 100 μm. A thickness of each of the electrodes is usually in a range of 1 nm to 1 μm, preferably in a range of 5 nm to 0.5 nm, more preferably in a range of 10 nm to 0.2 μm. The source 1, the drain 2, and the gate electrode 3a are wired respectively. The wiring is made from a material that is substantially the same as the source 1, the drain 2, and the gate electrode 3a.

The dielectric layer 5 is made from a material having insulation properties. Examples of the material encompass: polymers (polyparaxylylene, polyacrylate, polymethylmethacrylate, polystyrene, polyvinylphenol, polyamide, polyimide, polycarbonate, polyester, polyvinylalcohol, polyvinyl acetate, polyurethane, polysulphone, epoxy resin, and phenol resin, for example) and copolymers made by combining these polymers; metal oxides (silica dioxide, aluminum oxide, titanic oxide, and tantalum oxide, for example); ferroelectric metal oxides ($SrTiO_3$ and $BaTiO_3$, for example); nitrides (silicon nitride and aluminum nitride, for example); sulfides; dielectrics (fluoride, for example); and polymers in which particles of these dielectrics are dispersed. A thickness of the dielectric layer 5 differs depending on its material. However, the thickness is usually in a range of 0.1 nm to 100 μm, preferably in a range of 0.5 nm to 50 μm, more preferably in a range of 1 nm to 10 μm. The method of forming the dielectric layer 5 is as described above.

The organic semiconductor material 6 is as described above. A thickness of the organic semiconductor material 6 is in a range of 1 nm to 10 μm, preferably in a range of 5 nm to 5 μm, more preferably in a range of 10 nm to 3 μm.

In the thin film transistor device of the preset invention, it is possible to provide another layer as appropriate, for example, between the substrate and the dielectric layer, between the dielectric layer and the organic semiconductor material layer, and/or on an outer surface of the device. For example, if a protection layer is provided on the organic semiconductor material layer directly or via another layer, it is possible to reduce an influence from the open air such as humidity. Further, it is also possible to attain a stable electrical property, e.g., a greater on/off ratio of the device.

A material of the protection layer is not particularly limited. However, the protection layer is preferably made from: a film made from a resin such as acryl resin (epoxy resin, or polymethyl methacrylate, for example), polyurethane, polyimide, polyvinylalcohol, fluorine resin, or polyolefin; an inorganic oxide film (silicon oxide, aluminum oxide, or silicon nitride, for example); and a film made from a dielectric (nitride film, for example). A resin (polymer) that has low transmittance or low absorbability with respect to oxygen or water is particularly preferable. It is also possible to use a protection material, which has been developed for an organic EL display in recent years. A thickness of the protection film can be determined arbitrarily in accordance with its usage. However, the thickness is usually in a range of 100 nm to 1 mm.

In the exemplary devices described above, any of the layers (such as the substrate layer and the dielectric layer, and the dielectric layer and the organic semiconductor material layer) may be provided by employing a vacuum deposition method, a sputtering method, a coating method, a printing method, a sol-gel method, or the like method as appropriate, for example.

Figure 3:
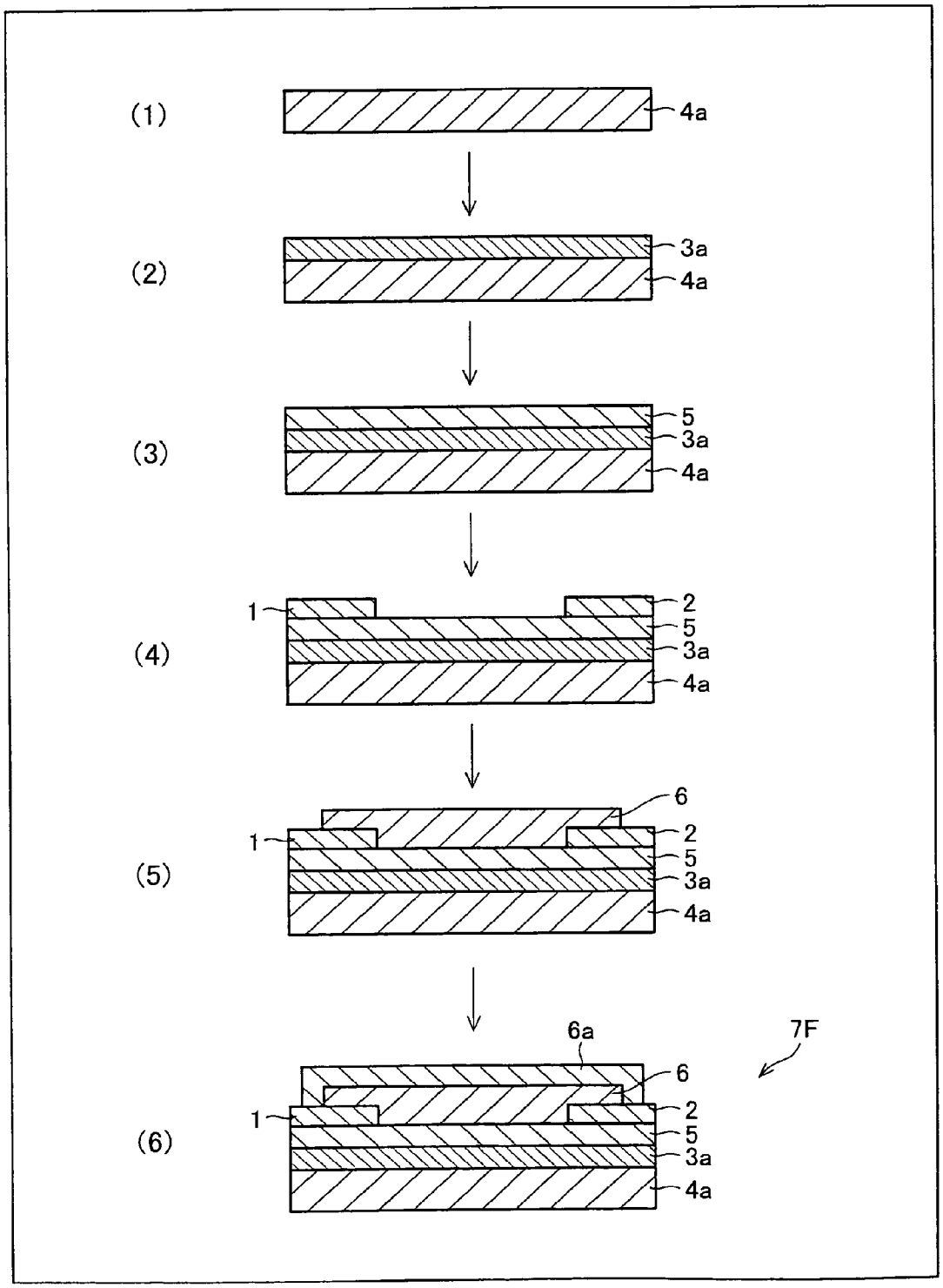
FIG. 3 is a cross sectional view schematically illustrating assembling steps of an organic semiconductor device according to an embodiment of the present invention.

Next, with reference to FIG. 3, the following describes a method of manufacturing a thin film transistor device of the present invention, by referring to, as an example, a bottom-contact type thin film transistor device illustrated in the exemplary embodiment A in FIG. 2.

This manufacturing method is also applicable to the other exemplary thin film transistor devices.

(Substrate and Substrate Treatment)

The thin film transistor device of the present invention is manufactured by providing necessary various layers and electrodes on the substrate 4a (see (1) of FIG. 3). The substrate 4a is as described above, but the substrate 4a may have a function of an electrode, if necessary.

(Formation of Gate Electrode)

The gate electrode 3a is formed on the substrate 4a (see (2) of FIG. 3). The gate electrode 3a is made from a material as described above. An electrode film can be formed by various methods. Examples of the method encompass a vacuum deposition method, a sputtering method, a coating method, a thermal transfer method, a printing method, and a sol-gel method. During or after the film formation, patterning is preferably carried out, as appropriate, so as to form the film in a desired shape. As a method of carrying out the patterning, various methods can be adopted. Examples of the patterning method encompass a photolithographic method in which patterning and etching of a photoresist are carried out in combination. Further, the patterning can be carried out by: a printing method (an ink jet printing method, a screen printing method, an offset printing method, or a letterpress method, for example); a soft lithographic method (a micro-contact printing method, for example); or a method in which some of these methods are carried out in combination. A thickness of the gate electrode 3a differs depending on its material. However, the thickness is usually in a range of 0.1 nm to 10 μm, preferably in a range of 0.5 nm to 5 μm, more preferably in a range of 1 nm to 3 μm. Furthermore, in a case where the gate electrode 3a and the substrate 4a are formed as a single member, it is possible to have the thickness longer than the above values.

(Formation of Dielectric Layer)

Next, the dielectric layer 5 is formed on the gate electrode 3a (see (3) of FIG. 3). A material of the dielectric layer 5 is as described above. In order to form the dielectric layer 5, various methods can be used. Examples of the method encompass: a coating method (a spin coating method, a spray coating method, a dip coating method, a cast method, a bar-coating method, or a blade coating method, for example); a printing method (a screen printing method, an offset printing method, or an ink jet printing method, for example); and a dry process method (a vacuum deposition method, a molecular beam epitaxial growth method, an ion cluster beam method, an ion plating method, a sputtering method, an atmospheric-pressure plasma method, or a CVD method, for example). Other than these methods, the method may be a sol-gel method, or a method of providing an oxide film on a metal (alumite provided on aluminum, or silicon oxide provided on silicon, for example).

(Formation of Source Electrode and Drain Electrode)

The source electrode 1 and the drain electrode 2 can be formed by the method of forming the gate electrode 3a, or a method based on the method of forming the gate electrode 3a (see (4) of FIG. 3).

(Formation of Organic Semiconductor Material Layer)

The organic semiconductor material has been already described above, and a method of forming the organic semiconductor material has been also described above.

(Formation of Protection Layer)

The protection layer 6a formed on the organic semiconductor material 6 makes it possible to (i) keep the influence from the open air at a minimum, and (ii) stabilize the electrical property of the organic thin film transistor device, as described above (see (6) of FIG. 3). The protection layer 6a may be made from the aforementioned materials.

In order to form the protection layer 6a, various methods can be adopted. For example, in a case where the protection layer is made from a resin, the method may be, for example, (i) a method in which a resin solution is applied, and then dried, so as to form a resin film, or (ii) a method in which a resin monomer is either applied or vapor-deposited, and then polymerized. It is also possible to perform a cross-linking treatment after the film is formed. In a case where the protection layer 6a is made from an inorganic material, it is possible to form the film in a vacuum process (a sputtering method, or a vapor deposition method, for example), or in a solution process (a sol-gel method, for example).

The thin film transistor device of the present invention may be provided with a protection film not only on the organic semiconductor material layer but also between each of the layers, if necessary. In some cases, these layers can be of help to stabilization of the electrical property of the organic thin film transistor device.

Thus, an object of the present invention is to provide (i) a novel fused polycyclic aromatic compound that can satisfy both a high electron field-effect mobility and a high on/off current ratio, both of which are required in an organic semiconductor material, and (ii) a high performance organic semiconductor device employing the fused polycyclic aromatic compound.

The present invention will be described more specifically with Examples as below. However, the present invention is not limited to the examples.

EXAMPLES

In Examples, various measurements were carried out with respect to obtained compounds: melting point measurement was carried out by use of Yanagimoto micro melting point apparatus; TG/DTA (differential thermal analysis) was carried out by use of TG/DTA 6200 (made by Seiko Instruments Inc.); $^1$H-NMR and $^{13}$C-NMR measurement was carried out by use of LAMBDA-400 (made by JEOL Ltd.); IR measurement was carried out by use of FTIR-8100 (made by Shimazu Corporation); mass analysis was carried out by use of GCMS-QP 5050 type mass analyzer; elemental analysis was carried out by use of 2400 CHN type elemental analyzer (made by Perkin Elmer Japan).

Example 1

(1-1) Synthesis of 3-methylthio-2-naphthaldehyde

N,N,N'-trimethylethylenediamine (2.87 ml, 21.0 mmol) and anhydrous tetrahydrofuran (35 ml) were added, in nitrogen gas stream, into a 100 ml three-neck flask equipped with a dropping funnel, and were cooled down to −30° C. Then, a 1.59M butyllithium hexane solution (13.21 ml, 21.0 mmol) maintained at −30° C. was added into the three-neck flask, and an obtained reaction solution was stirred for 15 minutes. After that, an anhydrous tetrahydrofuran (10 ml) solution of 2-naphthaldehyde (2.00 g, 12.8 mmol) maintained at −30° C. was dropped into the flask over 5 minutes, and the reaction solution was stirred for 15 minutes.

Further, after a 1.59 M butyllithium hexane solution (24.15 ml, 38.4 mmol) was added into the reaction solution maintained at −30° C., the reaction solution was stirred for 3.5 hours. Dimethyldisulfide (5.67 ml, 64 mmol) was added into the reaction solution maintained at −30° C., and the reaction solution was stirred for 2 hours at a room temperature. Then, approximately 20% hydrogen chloride was added to the reaction solution, and the reaction solution was stirred for 10 hours.

Thus obtained reaction solution was extracted with methylene chloride, and then a resultant organic layer was dried with anhydrous magnesium sulfate and filtrated. A solvent was removed by use of a rotary evaporator. An obtained crude product was purified by silica gel column chromatography (carrier: hexane-ethyl acetate (9:1)), so as to obtain a component of Rf 0.3 as a yellow liquid. Then, a solvent of the yellow liquid was evaporated off so as to obtain 2-methylthio-3-naphthaldehyde (1.49 g, 7.37 mmol, yield 58%) as a yellow solid.

mp 53.5-54.5° C.; $^1$H NMR (400 MHz, CDCl$_3$) δ 2.60 (s, 3H, SMe), 7.49 (ddd, 1H, J=8.1, 8.1, 1.2 Hz, ArH), 7.60 (s, 1H, ArH), 7.62 (ddd, 1H, J=8.2, 8.2, 1.2 Hz, ArH), 7.79 (d, 1H, J=8.2 Hz, ArH), 7.92 (d, 1H, J=8.2 Hz, ArH), 8.32 (s, 1H, ArH), 10.35 (s, 1H, CHO); $^{13}$C NMR (100 MHz, CDCl$_3$) δ 15.1, 122.7, 125.7, 126.4, 128.9, 129.2, 129.4, 130.8, 135.5, 136.4, 136.9, 191.3; IR (KBr) ν 1699 (C=O), 1620, 1433, 1169, 1026, 872, 776, 756 cm$^{-1}$; EIMS (70 eV) m/z=202 (M$^+$); Anal. Calcd for C$_{12}$H$_{10}$OS: C, 71.25; H. 4.98%. Found: C, 71.05; H, 4.83%.

(1-2) Synthesis of 1,2-bis(3-methylthio-2-naphthyl)ethylene

Zinc powder (0.392 g, 6.0 mmol) and anhydrous tetrahydrofuran (10 ml) were added, in nitrogen gas stream, into a 100 ml two-neck flask equipped with a reflux cooling tube, and were cooled down in ice bath. After titanium tetrachloride (0.66 ml, 6.0 mmol) was slowly dropped into the two-neck flask, a reaction was carried out at a reflux temperature for 1.5 hours. After that, the temperature in the two-neck flask was brought back to a room temperature, a tetrahydrofuran (10 ml) solution of 2-methylthio-3-naphthaldehyde (0.405 g, 2.0 mmol) was slowly dropped into the two-neck flask, and a reaction was carried out at a reflux temperature for 10 hours.

After the temperature of the two-neck flask was cooled down to the room temperature, a saturated sodium carbonate aqueous solution (approximately 30 ml) and methylene chloride (approximately 30 ml) were added into the two-neck flask and stirred for 3.5 hours. An obtained solution was filtrated so that an insoluble solid in the flask was removed. Thus obtained filtrate solution was extracted with methylene chloride, and then a resultant organic layer was dried with anhydrous magnesium sulfate and evaporated. An obtained crude product was purified by silica gel column chromatography (developing solvent: methylene chloride) so as to obtain 1,2-di(2-methylthio-3-naphthyl)ethylene (0.299 g, 0.80 mmol, yield 80%) as a yellow solid.

yellow crystals; mp 195.0-196.0° C.; $^1$H NMR (400 MHz, CDCl$_3$) δ 2.60 (s, 6H, SMe), 7.43 (ddd, 2H, J=7.4, 7.4, 1.7 Hz, ArH), 7.46 (ddd, 2H, J=7.6, 7.6, 1.7 Hz, ArH), 7.64 (s, 2H, ArH), 7.66 (s, 2H, CH=CH), 7.75 (d, 2H, J=8.0 Hz, ArH), 7.85 (d, 2H, J=8.0 Hz, ArH), 8.10 (s, 2H, ArH); $^{13}$C NMR (100 MHz, CDCl$_3$) δ 16.3, 124.1, 125.2, 125.6, 126.45, 126.54, 127.9, 128.5, 131.5, 133.4, 134.9, 135.9; IR (KBr) ν 1485, 1426, 1024, 957, 862, 741 cm$^{-1}$; EIMS (70 eV) m/z=372 (M$^+$), 357 (M$^+$-Me), 325 (M$^+$-SMe); Anal. Calcd for C$_{24}$H$_{20}$S$_2$: C, 77.37, H, 5.41%. Found, 77.07; H, 5.26%.

(1-3) Synthesis of dinaphtho[2,3-b:2',3'-f]thieno[3,2-b]thiophene

Into a 50 ml round-shaped flask equipped with a reflux tube, 1,2-di(2-methylthio-3-naphthyl)ethylene (0.2235 g, 0.60 mmol), iodine (4.8731 g, 19.20 mmol), and chloroform (15 ml) were added, and an obtained reaction solution was refluxed for 21 hours. After the reaction solution was cooled down to a room temperature, a saturated sodium hydrogensulfite aqueous solution (approximately 20 ml) was added to the reaction solution. An insoluble solid was filtered out therefrom and washed with chloroform and water. An obtained yellow solid was purified by sublimation so as to obtain dinaphtho[2,3-b:2',3'-f]thieno[3,2-b]thiophene (0.1730 g, 0.51 mmol, yield 85%) as a yellow solid. A melting point of the obtained compound was not correctly measured because the compound has a sublimation property at temperatures of not less than 300° C. For this reason, the melting point was measured by TG/DTA.

yellow crystals; melting point about 425° C. (TG-DTA measurement); $^1$H NMR (400 MHz, CDCl$_3$) δ 7.54-7.57 (m, 4H, ArH), 7.96-7.98 (m, 2H, ArH), 8.05-8.07 (m, 2H, ArH), 8.40 (s, 2H, ArH), 8.45 (s, 2H, ArH); IR (KBr) ν 1273, 872, 750, 739 cm$^{-1}$; EIMS (70 eV) m/z=340 (M$^+$), 170 (M$^+$/2); Anal. Calcd for C$_{22}$H$_{12}$S$_2$: C, 77.61; H, 3.55%. Found: C, 77.40; H, 3.38%.

Example 2

(2-1) Synthesis of 3-methylseleno-2-naphthaldehyde

N,N,N'-trimethylethylenediamine (2.87 ml, 21.0 mmol) and anhydrous tetrahydrofuran (35 ml) were added, in nitrogen gas stream, into a 100 ml three-neck flask equipped with a dropping funnel, and were cooled down to –40° C. Then, a butyllithium hexane solution (1.59M, 13.2 ml, 21.0 mmol) was added into the three-neck flask at –40° C., and an obtained reaction solution was stirred for 20 minutes. After that, an anhydrous tetrahydrofuran (10 ml) solution of 2-naphthaldehyde (2.00 g, 12.8 mmol) was dropped into the flask at –40° C. over 10 minutes, and the reaction solution was stirred for 70 minutes. Further, after a butyllithium hexane solution (1.59 M, 24.15 ml, 38.4 mmol) was added into the reaction solution at –40° C., the reaction solution was stirred for 3 hours. Selenium powder (3.03 g, 38.4 mmol) was added into the reaction solution at –40° C., and the reaction solution was stirred for 10 minutes at a room temperature. Thereafter, methyl iodide (2.49 ml, 40.9 mmol) was added into the reaction solution over 10 minutes, and the reaction solution was further stirred for 1 hour at the room temperature. Then, approximately 20% hydrogen chloride was added to the reaction solution, and the reaction solution was stirred for 4 hours. Thus obtained reaction solution was extracted with methylene chloride, and then a resultant organic layer was dried with anhydrous magnesium sulfate and filtrated. A solvent was removed by use of a rotary evaporator. Thus obtained reaction mixture was separated and purified by silica gel column chromatography by use of a mixture solvent of hexane and ethyl acetate (hexane:ethyl acetate=9:1) as a mobile phase, so as to obtain a yellow liquid. The yellow liquid was left to stand, thereby preparing 3-methylseleno-2-naphthaldehyde (1.01 g, 4.05 mmol, 32%) as a yellow solid.

$^1$H NMR (400 MHz, CDCl$_3$) δ 2.37 (s, 3H, SeMe (d, $J_2{}^{77}{}_{Se}{}^{-1}{}_H$=13.5 Hz)), 7.50 (ddd, 1H, J=8.2, 8.2, 1.3 Hz, ArH), 7.62 (ddd, 1H, J=8.1, 8.1, 1.4 Hz, ArH), 7.69 (s, 1H, ArH), 7.77 (dd, 1H, J=8.1, 1.0 Hz, ArH), 7.91 (dd, 1H, J=8.1, 0.6 Hz, ArH), 8.26 (s, 1H, ArH), 10.22 (d, 1H, J=0.8 Hz, CHO); $^{13}$C NMR (100 MHz, CDCl$_3$) δ 5.9, 126.08, 126.12, 126.7, 129.1, 129.8, 130.0, 131.5, 132.6, 136.0, 138.3, 192.5; IR (KBr) ν 1684 (C=O), 1671, 1624, 1445, 1253, 1171, 1005, 882, 776, 741 cm$^{-1}$; EIMS (70 eV) m/z=250 (M$^+$).

(2-2) Synthesis of 1,2-di(3-methylseleno-2-naphthyl)ethylene

Zinc powder (0.406 g, 6.21 mmol) and anhydrous tetrahydrofuran (10 ml) were added, in nitrogen gas stream, into a 100 ml two-neck flask equipped with a reflux tube, and were cooled down in ice bath. After titanium tetrachloride (0.684 ml, 6.21 mmol) was slowly dropped into the two-neck flask, pyridine (0.056 ml, 0.690 mmol) was added into the flask, and a resultant was refluxed for 1.5 hours. Then, a tetrahydrofuran (10 ml) solution of 3-methylseleno-2-naphthaldehyde (0.516 g, 2.07 mmol) was dropped into the flask over 10 minutes, and an obtained solution was refluxed for 7 hours. After the solution was cooled down to a room temperature, a saturated sodium hydrogen carbonate aqueous solution (approximately 10 ml) and chloroform (approximately 30 ml) were added to the solution, and the solution was stirred for 10 hours. The solution was filtrated so that an insoluble solid was removed. An obtained filtrate solution was extracted with chloroform, and then a resultant organic layer was dried with anhydrous magnesium sulfate and filtrated. A solvent was removed by use of a rotary evaporator. Thus obtained reaction mixture was recrystallized with the use of chloroform and hexane so as to obtain 1,2-di(3-methylseleno-2-naphthyl)ethylene (0.194 g, 0.416 mmol, 40%) as light yellow crystalline powder.

mp 199.0-199.5° C.; $^1$H NMR (400 MHz, CDCl$_3$) δ 2.44 (s, 6H, SeMe (d, $J_2{}^{77}{}_{Se}{}^{-1}{}_H$=11.5 Hz)), 7.44-7.49 (m 4H, ArH), 7.63 (s, 2H, ArH), 7.75-7.76 (m, 2H, ArH), 7.86-7.88 (m, 4H, ArH and CH=CH), 8.10 (s, 2H, ArH); $^{13}$C NMR (100 MHz, CDCl$_3$) δ 7.8, 125.1, 125.9, 126.4, 126.6, 127.9, 128.9, 130.4, 130.7, 132.2, 133.4, 136.5; IR (KBr) ν 1487, 1424, 951, 862, 747, 735 cm$^{-1}$; EIMS (70 eV) m/z=468 (M$^+$, $^{80}$Se×2), 466 (M$^+$, $^{80}$Se+$^{78}$Se); Anal. Calcd for C$_{24}$H$_{20}$Se$_2$: C, 61.81; H, 4.32. Found: C, 61.82; H, 4.29.

(2-3) Synthesis of dinaphtho[2,3-b:2',3'-f]selenopheno[3,2-b]selenophene

Into a 20 ml round-shaped flask, 1,2-di(3-methylthio-2-naphthyl)ethylene (0.192 g, 0.412 mmol), iodine (3.35 g, 13.2 mmol), and chloroform (10 ml) were added. A reflux tube was attached to the flask, and an obtained reaction solution was refluxed for 15 hours. After the reaction solution was cooled down to a room temperature, a saturated sodium hydrogensulfite aqueous solution (approximately 5 ml) was added to the reaction solution. An insoluble solid was filtered out therefrom and washed with chloroform and water. An obtained yellow solid was purified twice by temperature gradient sublimation so as to obtain dinaphtho[2,3-b:2',3'-f]selenopheno[3,2-b]selenophene (0.140 g, 0.322 mmol, 78%) as yellow crystalline powder.

mp>300° C.; $^1$H NMR (400 MHz, CDCl$_3$) δ 7.53-7.57 (m, ArH), 7.91-7.94 (m, ArH), 8.01-8.03 (m, ArH), 8.29 (s, ArH), 8.45 (s, ArH); IR (KBr) ν 1418, 1271, 1256, 874, 752 cm$^{-1}$; EIMS (70 eV) m/z=436 (M$^+$, $^{80}$Se×2), 434 (M$^+$, $^{78}$Se+$^{78}$Se); Anal. Calcd for C$_{22}$H$_{12}$Se$_2$: C, 60.85; H, 2.79. Found: C, 60.56; H, 2.60.

Example 3

Manufacturing of FET Device

With the use of a compound synthesized in accordance with Example 1 as an organic semiconductor material 6, an FET device (organic semiconductor device) having a structure shown in FIG. 1 was manufactured.

More specifically, an organic semiconductor device 7 was manufactured as follows. Dinaphtho[2,3-b:2',3'-f]thieno[3,2-b]thiophene was deposited, by vacuum deposition, on a silicon substrate (a substrate 4) in which a silicon oxide (a dielectric layer 5, $SiO_2$) was formed, by thermal oxidation, on an n-doped silicon wafer so as to have a thickness of 200 nm. Then, with the use of a shadow mask, a source 1 and a drain 2 were formed thereon by a vacuum deposition method or an electron beam drawing method (EB method). The source 1 and the drain 2 had a width of 1.5 mm, and a space between the source 1 and the drain 2 was 0.05 mm.

How the substrate temperature affected performances of an obtained element was evaluated at three different temperatures (a room temperature, 60° C., and 100° C.) of the silicon substrate in deposing the organic semiconductor material 6 on the dielectric layer 5. Substrates 4 used for manufacturing FET devices were three types: (i) a substrate in which a surface of the dielectric layer 5 was treated with a toluene solution of octyltrichlorosilane (OTS) as a silane coupling agent before the organic semiconductor material was deposited on the silicon substrate; (ii) a substrate (HMDS) in which a surface of the dielectric layer 5 was treated with hexamethyldisilazane (HMDS) vapor before the organic semiconductor material was deposited on the silicon substrate; and (iii) a substrate (bare $SiO_2$) in which a surface of the dielectric layer 5 was not treated by these treatments. At least ten FET devices were produced for each of the conditions. Table 1 shows data on how successfully reproducibility of each of the FET devices was exhibited.

TABLE 1

| | $T_{sub}$/° C. | $\mu_{FET}/cm^2 V^{-1} s^{-1}$ | $I_{on}/I_{off}$ |
|---|---|---|---|
| bare $SiO_2$ | rt | 0.08-0.12 | $5 \times 10^6$ |
| bare $SiO_2$ | 60 | 0.15-0.26 | $5 \times 10^5$ |
| bare $SiO_2$ | 100 | $6.3-8.5 \times 10^{-5}$ | $10^5$ |
| HMDS | rt | 0.62-0.68 | $5 \times 10^6$ |
| HMDS | 60 | 0.86-0.89 | $5 \times 10^6$ |
| HMDS | 100 | 0.73-0.93 | $10^7$ |
| OTS | rt | 0.84-1.2 | $5 \times 10^6$ |
| OTS | 60 | 1.2-1.7 | $10^7$ |
| OTS | 100 | 1.0-1.3 | $10^7$ |

In table 1, Tsub./° C. indicates a temperature condition of the silicon substrate, μFET indicates an electron field effect mobility of the FET device, and $I_{on}/I_{off}$ indicates an on/off ratio. Table 1 demonstrated that the semiconductor devices produced in Example 3 had good on/off ratios. Especially, it was demonstrated that the FET device manufactured under the conditions in which the OTS treatment was carried out and a substrate temperature was 60° C., had an electron field effect mobility of not less than 1.2 $cm^2V^{-1}S^{-1}$ but not more than 1.7 $cm^2V^{-1}S^{-1}$. This value of the electron field effect mobility of the FET device achieves the highest level among those of devices using organic semiconductor materials which have been reported so far. This proves that the dinaphtho[2,3-b: 2',3'-f]thieno[3,2-b]thiophene is a notably excellent semiconductor material.

Figure 4:
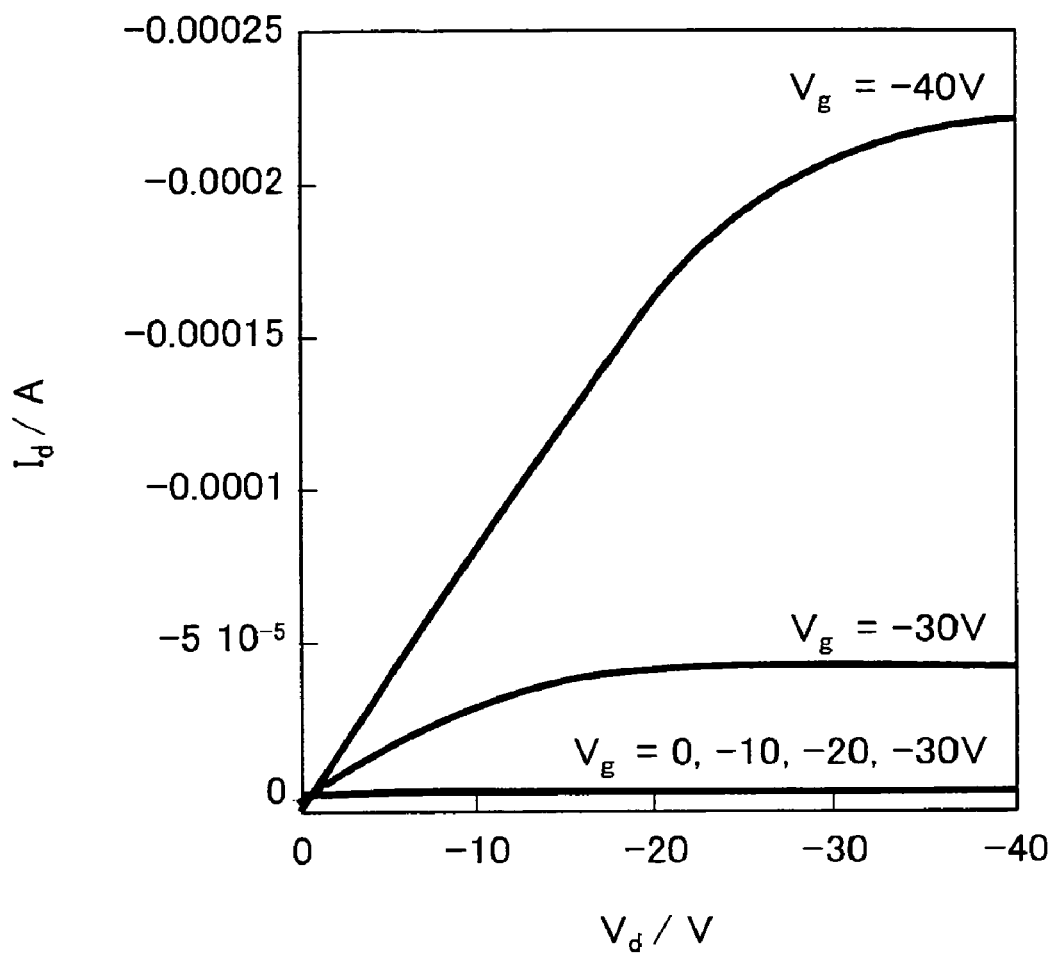
FIG. 4 is graphs showing FET response curves of an organic semiconductor device using dinaphtho[2,3-b:2',3'-f]thieno[3,2-b]thiophene.

FIG. 4 shows FET response curves obtained by the FET device manufactured in the present example. Calculation of electron field-effect mobility of a semiconductor was carried out based on description of "Semiconductor Device: Physics and Technology" (Sze, S. M., pp 30-35, pp 200-207 (1985)). FIG. 4 shows output characteristics of the FET device manufactured, at a temperature condition of 60° C., by use of a substrate whose surface was treated with OTS. The output characteristic means an Id–Vd characteristic between a source and a drain, and the characteristic was measured while a gate voltage was increased in multiple stages. FIG. 4 demonstrates that Id levels off at a high Vd region (a level-off region), which exhibits a typical FET behavior. Further, FIG. 4 demonstrates that Id linearly rises at a low Vd region (a linear region), which exhibits a successful contact between a semiconductor and electrodes.

Figure 5:
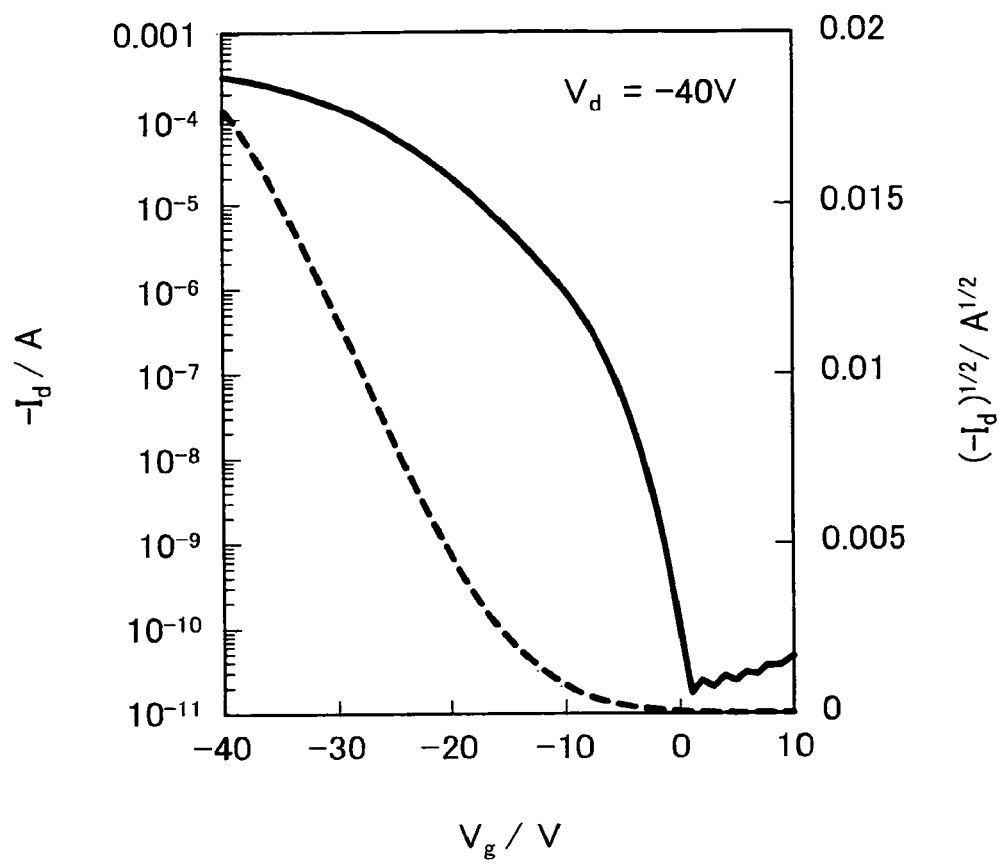
FIG. 5 is graphs showing transfer curves of an organic semiconductor device (a substrate temperature of 60° C. for vapor deposition) using dinaphtho[2,3-b:2',3'-f]thieno[3,2-b]thiophene.

Further, FIG. 5 shows a transfer characteristic of the organic semiconductor device 7 produced in the present example. In FIG. 5, a graph in full line indicates Id (drain current, indicated by a left scale), a graph in dotted line indicates a square root of an absolute value of the drain current (indicated by a right scale), and Vd indicates a low gate voltage. Further, a transfer characteristic of the organic semiconductor device of the present invention that had been stored in the atmosphere for 6 months was also measured. The measurement result demonstrated that the transfer characteristic had almost the same values as those measured immediately after the device was manufactured, which proved that the organic semiconductor device of the present invention was highly durable.

Example 4

Bottom-Contact Type FET

A resist material was applied to an n-doped silicon wafer including a thermal oxidation film ($SiO_2$) with a thickness of 300 nm which thermal oxidation film had been treated with hexamethyldisilazane (HMDS), exposed and patterned. Then, chrome was deposited on the patterned n-doped silicon wafer so as to have a thickness of 1 nm, and further gold was deposited thereon so as to have a thickness of 40 nm.

After that, the resist was removed so as to form a source electrode (1) and a drain electrode (2). The electrodes were interleave electrodes having twenty channels of 25 μm in channel length and 2 mm in channel width.

Electrodes were formed in the aforementioned manner on the following substrates, similarly to Example 3: a substrate (bare $SiO_2$) in which a surface of a dielectric layer 5 was not treated by any treatments; and a substrate (HMDS) in which a surface of a dielectric layer 5 was treated with hexamethyldisilazane (HMDS) were used. The substrates were placed in a vacuum deposition apparatus, and the apparatus was evacuated until a degree of vacuum became not more than $1.0 \times 10^{-3}$ Pa. A compound synthesized in Example 1 was deposited, by a resistance heating deposition method, on each of the substrates so as to have a thickness of 50 nm. A substrate temperature was 60° C. In this way, a layer of the organic semiconductor material 6 was formed. Herewith, a field effect transistor of the present invention was obtained.

As illustrated in A of FIG. 2, in each of the organic field effect transistors of the present example, the n-doped silicon wafer including the thermo oxidation film was such that the thermo oxidation film functioned as a dielectric layer 5 and the n-doped silicon wafer functioned as a substrate and a gate electrode.

Table 2 shows data of the FET devices, similarly to Table 1.

TABLE 2

| | $T_{sub}$/° C. | $\mu_{FET}/cm^2 V^{-1} s^{-1}$ | $I_{on}/I_{off}$ |
|---|---|---|---|
| bare $SiO_2$ | 60 | 0.26-0.33 | $1 \times 10^4$ |
| HMDS | 60 | 0.96-1.0 | $5 \times 10^5$ |

The material of the present example exhibits the highest mobility among those of the bottom-contact type thin film transistors that have been reported so far. A structure of the bottom-contact type is preferable in view of forming a highly precise device because source and drain electrodes can be formed before the organic semiconductor material 6 is formed. The examination clearly demonstrated the superiority of the semiconductor material of the present invention in the current situation in which creation of excellent materials is required.

Example 5

(5-1) Synthesis of 6-methyl-2-naphthaldehyde

The following deals with synthesis of 6-methyl-2-naphthaldehyde represented by Chemical Formula (21).

Chem. 48

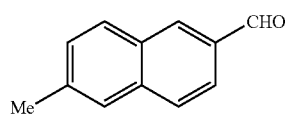
(21)

Into a 500 ml three-neck flask, 2,6-dimethylnaphthalene (5.0 g, 32 mmol), NBS (N-bromosuccinimide) (5.7 g, 32 mmol), and $CCl_4$ (200 ml) were added and dissolved. An obtained solution was deaerated by nitrogen gas for 15 minutes. The solution was then refluxed for 1 hour while being irradiated with infrared lamp. After that, the solution was cooled down to a room temperature, and a solid was filtered out. An obtained filtrate solution was concentrated by use of a rotary evaporator so as to obtain a white solid (9.3 g). Further purification was not carried out, and the obtained white solid was used in a subsequent reaction.

Thus obtained crude mixture (9.3 g) of 2-bromomethyl-6-methylnaphthalene and DMSO (dimethylsulfoxide) (65 ml) were added into a 200 ml three-neck flask equipped with a Dean-Stark dehydrator and a reflux tube, and were heated for 5 hours at 100° C. Then, water (65 ml) was added thereto. An obtained reaction solution was extracted with ethyl acetate, and a resultant organic layer was washed out with a saline solution and dried with anhydrous magnesium chloride. After the drying agent was filtered off, a filtrate was concentrated by use of a rotary evaporator. A resultant residue was purified by silica gel column chromatography (solvent: methylene chloride, column diameter: 3 cm, column length: 20 cm) so as to obtain 6-methyl-2-naphthaldehyde (2.5 g, 16.5 mmol, 45%).

Mp. 110-111° C.; $^1$H NMR (400 MHz, $CDCl_3$) δ 2.56 (s, 3H, Me), 7.43 (dd, 1H, J=8.5, 1.64 Hz, ArH), 7.69 (s, 1H, ArH), 7.85 (d, 1H, J=8.39 Hz, ArH), 7.91 (d, 1H, J=7.88 Hz, ArH), 7.93 (dd, 2H, J=8.50, 1.58 Hz, ArH), 10.14 (s, 1H, CHO); EI-MS, m/z=170 ($M^+$).

(5-2) Synthesis of 6-methyl-3-methylthio-2-naphthaldehyde

The following deals with synthesis of 6-methyl-3-methylthio-2-naphthaldehyde represented by Chemical Formula (22).

Chem. 49

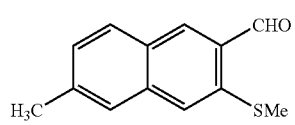
(22)

A 200 ml three-neck flask equipped with a dropping funnel was heated and dried, and air in the flask was replaced with nitrogen. N,N,N'-trimethyldiamine (1.22 ml, 9.6 mmol) and anhydrous THF (40 ml) were added into the flask and cooled down to −30° C. A butyllithium hexane solution (1.57 M, 6.14 ml, 9.6 mmol) was added thereto and stirred for 15 minutes. The temperature in the flask was brought back to −20° C., and an anhydrous THF (40 ml) solution of 6-methyl-2-naphthaldehyde (1.0 g, 5.9 mmol) was slowly dropped therein and stirred for 15 minutes. Further, after a butyllithium hexane solution (1.57 M, 11.2 ml, 0.017 mol) was added therein and stirred for 3.5 hours, dimethyldisulfide (2.6 ml, 0.029 mol) was added. The temperature was increased to a room temperature, and an obtained solution was stirred for 2 hours. Then, 1 M hydrogen chloride was added to stop the reaction, an obtained reaction solution was extracted with methylene chloride, and an organic layer was dried with anhydrous magnesium and filtrated. A filtrate was concentrated by use of a rotary evaporator. A residue was purified by silica gel column chromatography by use of a mixture solvent of hexane and ethyl acetate (hexane:ethyl acetate=9:1) as a mobile phase, so as to obtain 6-methyl-3-methylthio-2-naphthaldehyde (386 mg, 1.8 mmol, 30%) as a yellow solid.

Mp. 117-118° C.; $^1$H NMR (400 MHz, $CDCl_3$) δ 2.54 (s, 3H, Me), 2.58 (s, 3H, SMe), 7.33 (dd, 1H, J=8.40, 1.40 Hz, ArH), 7.53 (s, 1H, ArH), 7.58 (s, 1H, ArH), 7.83 (d, 1H, J=8.40 Hz, ArH), 8.28 (s, 1H); EI-MS, m/z=216 ($M^+$).

(5-3) Synthesis of 1,2-bis(6-methyl-3-methylthio-2-naphthyl)ethylene

The following deals with synthesis of 1,2-bis(6-methyl-3-methylthio-2-naphthyl)ethylene represented by Chemical Formula (23).

Chem. 50

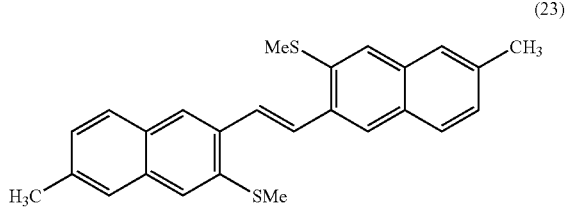
(23)

Air in a 200 ml three-neck flask equipped with a dropping funnel and a reflux tube was replaced with nitrogen, and THF (31 ml) was added into the three-neck flask. While the flask was being cooled in ice bath, $TiCl_4$ (0.35 ml, 3.2 mmol) was dropped into the flask, and subsequently zinc powder (209 mg, 3.2 mmol) was added therein. An obtained reaction solution was refluxed for 2 hours. After that, an anhydrous THF (15 ml) solution of 6-methyl-3-methylthio-2-naphthaldehyde (230 mg, 1.1 mmol) was slowly dropped into the reaction solution, and the reaction solution was refluxed for 20 hours. The reaction solution was then cooled down to a room temperature, a saturated sodium carbonate aqueous solution and chloroform were added thereto and stirred for 19 hours, and the reaction solution was filtrated so that an insoluble solid was removed. An obtained filtrate solution was extracted with chloroform, and a resultant organic layer was dried with anhydrous magnesium sulfate. A solvent was then removed therefrom by use of a rotary evaporator. An obtained yellow solid was separated and purified by silica gel column chromatography (methylene chloride solvent, column diameter: 3 cm, column length: 20 cm) so as to obtain 1,2-bis(6-methyl-3-methylthio-2-naphthyl)ethylene (131 mg, 0.33 mmol, 62%) as a yellow solid.

Mp. 185-186° C.; $^1$H NMR (400 MHz, $CDCl_3$) δ 2.51 (s, 6H, Me), 2.59 (s, 6H, SMe), 7.29 (dd, 2H, J=8.5, 1.9 Hz, ArH), 7.53 (s, 2H, ArH), 7.57 (s, 2H, ArH), 7.64 (s, 2H, olefin), 7.75 (d, 2H, J=8.5 Hz, ArH), 8.05 (s, 2H, ArH); EI-MS, m/z=400 ($M^+$).

(5-4) Synthesis of 2,9-dimethyldinaphtho[2,3-b:2',3'-f]thieno[3,2-b]thienophene The following deals with synthesis of 2,9-dimethyldinaphtho[2,3-b:2',3'-f]thieno[3,2-b]thienophene represented by Chemical Formula (24).

Chem. 51

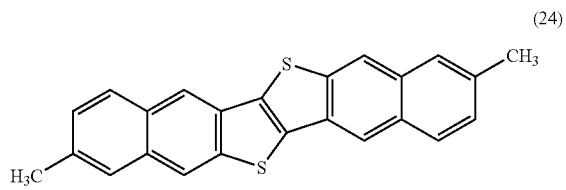

(24)

Into a 100 ml round-shaped flask, 1,2-bis(6-methyl-3-methylthio-2-naphthyl)ethylene (131 mg, 0.33 mmol), iodine (2.5 g, 9.8 mmol), and $CHCl_3$ (24 ml) were added, and an obtained reaction solution was refluxed for 22 hours. After the reaction solution was cooled down to a room temperature, a saturated sodium hydrogensulfite aqueous solution (100 ml) was added thereto so that excessive iodine was reduced. A resultant solution was extracted with $CHCl_3$. After a resultant organic layer was dried with anhydrous magnesium, a solvent was removed therefrom by use of a rotary evaporator. A resultant was recrystallized with chlorobenzene so as to obtain a yellow solid (19 mg, 0.05 mmol, 15%, only primary crystallization).

Mp. >300° C.; $^1$H NMR (270 MHz, $CD_2Cl_2$) δ 2.55 (s, 6H), 7.38 (dd, 2H, J=8.55, 1.64 Hz, ArH), 7.72 (s, 2H, ArH), 7.94 (d, 2H, J=8.55 Hz, ArH), 8.32 (s, 2H, ArH), 8.33 (s, 2H, ArH); EI-MS, m/z=368 ($M^+$).

With the use of thus obtained compound as an organic semiconductor material, an organic device was manufactured in the similar manner to Example 3. An obtained organic device exhibited a successful transfer characteristic similarly to the FET devices manufactured by use of the aforementioned materials of Examples 1 and 2.

Exemplary Synthesis 1

In order to check that a compound disclosed in Non Patent Literature 12, that is, a compound represented by Formula (XXI):

Chem. 52

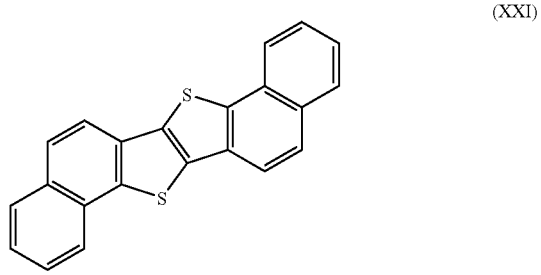

(XXI)

which compound is disclosed in Non Patent Literature 13, is different from the compound obtained in the aforementioned Example 1, the compound represented by Formula (XXI) was synthesized by the following method, and values of its physical properties were compared with those of the compound of Example 1. Non Patent Literature 13 discloses that the compound disclosed in Non Patent Literature 12 is not the compound represented by Formula (XIX), but correctly the compound represented by Formula (XXI).

The method for producing the compound represented by Formula (XXI) is as follows. N,N-dimethylformaldehyde (3.6 g) and sulfur (3.4 g, 0.11 mol) were added to a toluene solution (50 ml) of 2-naphthaldehyde (15.6 g, 0.10 mol). Thionyl chloride (36 ml) was added to an obtained solution, and a reaction temperature was maintained at 40° C. for 1 hour. After an inner temperature of the solution increased to 230° C., the temperature was maintained for 6 hours. Then, the solution was left to stand to cool so that the solution was cooled down to a room temperature. A precipitated solid was filtered out therefrom and washed with toluene and subsequently with acetone, so as to obtain a compound represented by Formula (XXI) (16.1 g, yield 43%).

EIMS (70 eV) m/z=340 ($M^+$), 170 ($M^+$/2)

Values of physical properties of (a) the dinaphtho[2,3-b:2',3'-f]thieno[3,2-b]thiophene obtained in Example 1 and (b) the compound represented by Formula (XXI) obtained in Exemplary Synthesis 1, and (c) the compound represented by Formula (XXI) disclosed in Non Patent Literature 13 were compared by measuring melting points of these compounds. Table 3 shows a comparison result. The melting points of the compounds obtained in Example 1 and Exemplary Synthesis 1 were measured by TG/DTA, and the melting point of the compound represented by Formula (XXI) (of Non Patent Literature 13) was referred to literature values.

TABLE 3

| Synthesis Method of Compound | Melting Point/° C. |
| --- | --- |
| Example 1 | 425 |
| Exemplary Synthesis 1 | 355 |
| Non Patent Literature 13 (literature value) | 350 |

Table 3 demonstrates that the melting points of the compound obtained in Exemplary Synthesis 1 and the compound represented by Formula (XXI) (Non Patent Literature 13) are almost identical, but they are different from that of the compound of Example 1, which proves that the compound of Example 1 is different from the compounds of Exemplary Synthesis 1 and Non Patent Literature 13.

Further, in the TG/DTA, the compound of Example 1 and the compound of Exemplary Synthesis 1 showed totally different tendencies. It was observed that the compound of Exemplary Synthesis 1 had two endothermic peaks at 332° C. and 355° C. By contrast, it was observed that the compound of Example 1 had only one endothermic peak at 425° C. This also proves that the compound of Example 1 is different from the compound of Exemplary Synthesis 1.

As a result, it is also demonstrated that the description of Non Patent Literature 13 is correct, that is, a structural formula of the compound disclosed in Non Patent Literature 12 is not the aforementioned Formula (2) as disclosed in Non Patent Literature 12, but actually Formula (XXI).

As described above, the compound of the present invention is (a) a compound including a BXBX skeleton further having an aromatic ring(s) located outside the BXBX skeleton, or (b) a compound including a BXBX compound in which a benzene ring is substituted with a heterocyclic ring. The compound(s) can strengthen an intermolecular interaction due to greater electron orbits. For this reason, with the use of the compound as a material of an organic semiconductor device, the electron field-effect mobility of an organic semiconductor can be improved, thereby resulting in that the compound can be successfully used as a very useful material to develop a new organic semiconductor device.

Further, with the method of the present invention for producing the compound, it is possible to easily produce, without multistage reactions, (a) the compound including a BXBX skeleton further having an aromatic ring(s) located outside the BXBX skeleton, or (b) the compound including a BXBX compound in which a benzene ring is substituted with a heterocyclic ring. Further, in the production method, impurities are hardly mixed into an obtained compound, thereby resulting in that a highly pure compound can be successfully obtained.

INDUSTRIAL APPLICABILITY

The compound of the present invention is hardly contaminated with impurities in its synthesizing process. This compound, once purified via sublimation, can achieve a mobility reaching 1.0 cm²/Vs and a high on/off ratio (maximum ratio: $10^7$) in an organic semiconductor device made by using the compound. The present invention enables easy production of various organic semiconductor materials having excellent electrical, electronic, or photoelectronic properties, which allows the materials to be widely used.

The invention claimed is:

1. A compound represented by General Formula (2):

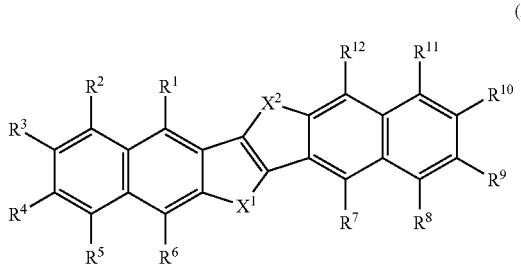

(2)

wherein $X^1$ and $X^2$ are both selenium or both sulfur; and $R^1$ through $R^{12}$ independently represent one atom or functional group selected from the group consisting of a hydrogen atom, a halogen atom, an alkyl group, an alkenyl group, an alkynyl group, an aryl group, an alkyloxy group, and an alkylthio group.

2. A compound represented by General Formula (3):

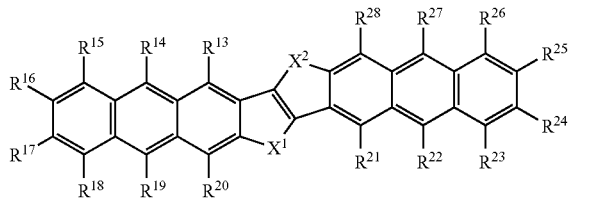

(3)

wherein $X^1$ and $X^2$ are both selenium or both sulfur; and $R^{13}$ through $R^{28}$ independently represent one atom or functional group selected from the group consisting of a hydrogen atom, a halogen atom, an alkyl group, an alkenyl group, an alkynyl group, an aryl group, an alkyloxy group, and an alkylthio group.

3. A compound represented by General Formula (4):

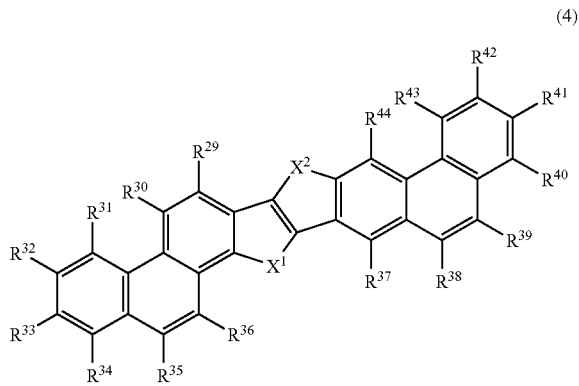

(4)

wherein $X^1$ and $X^2$ are both selenium or both sulfur; and $R^{29}$ through $R^{44}$ independently represent one atom or functional group selected from the group consisting of a hydrogen atom, a halogen atom, an alkyl group, an alkenyl group, an alkynyl group, an aryl group, an alkyloxy group, and an alkylthio group.

4. A method for producing a compound represented by General Formula (7):

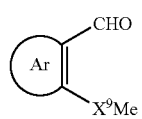

(7)

the compound being an intermediate of a compound as set forth in claim 1,
said method comprising the steps of:
(i) adding an alkyl metal reagent to a compound represented by General Formula (6):

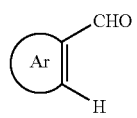

(6)

and (ii) after the step (i), adding dimethyl disulfide or dimethyl diselenide thereto, wherein in the formulae, $X^9$ represents selenium or sulfur; and
Ar represents a chemical structure represented by General Formula (10):

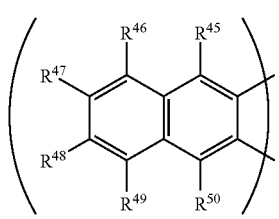

(10)

wherein $R^{45}$ through $R^{50}$ independently represent one atom or functional group selected from the group consisting of a hydrogen atom, a halogen atom, an alkyl group, an alkenyl group, an alkynyl group, an aryl group, an alkyloxy group, and an alkylthio group.

5. A method for producing a compound represented by General Formula (17):

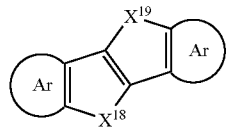

(17)

said method comprising the steps of:
(i) preparing compounds represented by General Formula (7) by a production method as set forth in claim 4;
(ii) reacting thus obtained compounds represented by General Formula (7) with each other, so as to obtain a compound represented by General Formula (16):

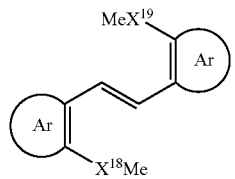

(16)

and (iii) reacting thus obtained compound represented by General Formula (16) with iodine,
wherein in the formulae, $X^{18}$ and $X^{19}$ are both selenium or both sulfur; and
each Ar represents a chemical structure represented by General Formula (10):

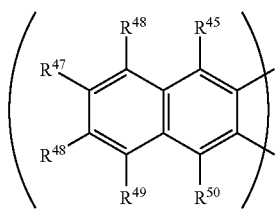

(10)

wherein $R^{45}$ through $R^{50}$ independently represent one atom or functional group selected from the group consisting of a hydrogen atom, a halogen atom, an alkyl group, an alkenyl group, an alkynyl group, an aryl group, an alkyloxy group, and an alkylthio group.

6. An organic semiconductor material comprising at least one compound as set forth in claim 1, 2 or 3.

7. An organic semiconductor device comprising an organic semiconductor material as set forth in claim 6.

8. The organic semiconductor device as set forth in claim 7, wherein the organic semiconductor device is a thin film transistor including an organic semiconductor layer.

9. The organic semiconductor device as set forth in claim 8, wherein the thin film transistor is a bottom-contact type field effect transistor.

10. The organic semiconductor device as set forth in claim 8, wherein the thin film transistor is a top-contact type field effect transistor.

11. The organic semiconductor device as set forth in claim 7, wherein the organic semiconductor device includes an organic carrier transporting layer and/or a light-emitting layer.

12. The organic semiconductor device as set forth in claim 7, wherein the organic semiconductor device has an electron field-effect mobility of not less than $1.0 \text{ cm}^2\text{V}^{-1}\text{s}^{-1}$ but not more than $1.7 \text{ cm}^2\text{V}^{-1}\text{s}^{-1}$.

13. The organic semiconductor device as set forth in claim 7, wherein the organic semiconductor device has an on/off current ratio of not less than $10^5$ but not more than $10^7$.

14. A method for producing a compound represented by General Formula (7):

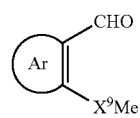

(7)

the compound being an intermediate of a compound as set forth in claim 2,
said method comprising the steps of:
(i) adding an alkyl metal reagent to a compound represented by General Formula (6):

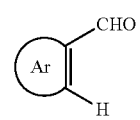

(6)

and (ii) after the step (i), adding dimethyl disulfide or dimethyl diselenide thereto, wherein in the formulae, $X^9$ represents selenium or sulfur; and
Ar represents a chemical structure represented by General Formula (11):

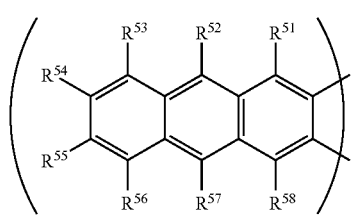

(11)

wherein $R^{51}$ through $R^{58}$ independently represent one atom or functional group selected from the group consisting of a hydrogen atom, a halogen atom, an alkyl group, an alkenyl group, an alkynyl group, an aryl group, an alkyloxy group, and an alkylthio group.

15. A method for producing a compound represented by General Formula (17):

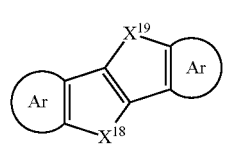

(17)

said method comprising the steps of:
(i) preparing compounds represented by General Formula (7) by a production method as set forth in claim 14;

(ii) reacting thus obtained compounds represented by General Formula (7) with each other, so as to obtain a compound represented by General Formula (16):

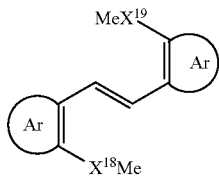

(16)

and (iii) reacting thus obtained compound represented by General Formula (16) with iodine,
wherein in the formulae, $X^{18}$ and $X^{19}$ are both selenium or both sulfur; and
each Ar represents a chemical structure represented by General Formula (11):

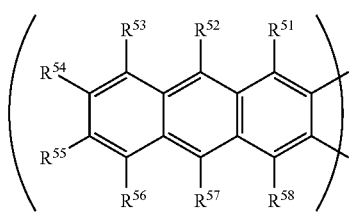

(11)

wherein $R^{51}$ through $R^{58}$ independently represent one atom or functional group selected from the group consisting of a hydrogen atom, a halogen atom, an alkyl group, an alkenyl group, an alkynyl group, an aryl group, an alkyloxy group, and an alkylthio group.

16. A method for producing a compound represented by General Formula (7):

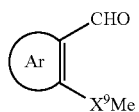

(7)

the compound being an intermediate of a compound as set forth in claim 3, said method comprising the steps of:
(i) adding an alkyl metal reagent to a compound represented by General Formula (6):

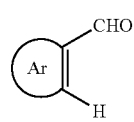

(6)

and (ii) after the step (i), adding dimethyl disulfide or dimethyl diselenide thereto, wherein in the formulae, $X^9$ represents selenium or sulfur; and Ar represents a chemical structure represented by General Formula (12):

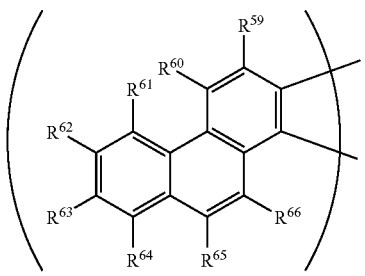

(12)

wherein $R^{59}$ through $R^{66}$ independently represent one atom or functional group selected from the group consisting of a hydrogen atom, a halogen atom, an alkyl group, an alkenyl group, an alkynyl group, an aryl group, an alkyloxy group, and an alkylthio group.

17. A method for producing a compound represented by General Formula (17):

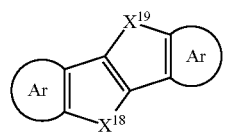

(17)

said method comprising the steps of:
(i) preparing compounds represented by General Formula (7) by a production method as set forth in claim 16;
(ii) reacting thus obtained compounds represented by General Formula (7) with each other, so as to obtain a compound represented by General Formula (16):

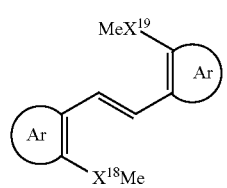

(16)

and (iii) reacting thus obtained compound represented by General Formula (16) with iodine,
wherein in the formulae, $X^{18}$ and $X^{19}$ are both selenium or both sulfur; and
each Ar represents a chemical structure represented by General Formula (12):

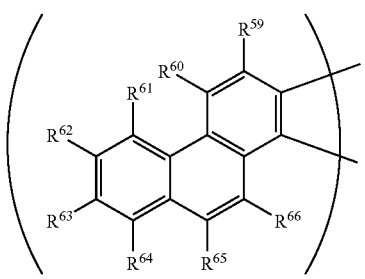

(12)

wherein $R^{59}$ through $R^{66}$ independently represent one atom or functional group selected from the group consisting of a hydrogen atom, a halogen atom, an alkyl group, an alkenyl group, an alkynyl group, an aryl group, an alkyloxy group, and an alkylthio group.

* * * * *

UNITED STATES PATENT AND TRADEMARK OFFICE
CERTIFICATE OF CORRECTION

PATENT NO.         : 8,232,546 B2
APPLICATION NO.    : 12/312083
DATED              : July 31, 2012
INVENTOR(S)        : Kazuo Takimiya and Tatsuya Yamamoto It is certified that error appears in the above-identified patent and that said Letters Patent is hereby corrected as shown below:

On the Title Page, Item [73] Assignee, "HIROSHIMA UNIVERSITY, CHIYODA-KU, TOKYO (JP)" should be changed to -- HIROSHIMA UNIVERSITY, HIGASHI-HIROSHIMA-SHI, HIROSHIMA (JP) and
   NIPPON KAYAKU KABUSHIKI KAISHA, CHIYODA-KU, TOKYO (JP) --.

Signed and Sealed this
Sixteenth Day of October, 2012

David J. Kappos
*Director of the United States Patent and Trademark Office*